United States Patent
Ooishi

(10) Patent No.: US 8,888,361 B2
(45) Date of Patent: Nov. 18, 2014

(54) CALORIFIC VALUE MEASURING SYSTEM AND CALORIFIC VALUE MEASURING METHOD

(75) Inventor: Yasuharu Ooishi, Tokyo (JP)

(73) Assignee: Azbil Corporation, Tokyo (JP)

( * ) Notice: Subject to any disclaimer, the term of this patent is extended or adjusted under 35 U.S.C. 154(b) by 176 days.

(21) Appl. No.: 13/462,132

(22) Filed: May 2, 2012

(65) Prior Publication Data

US 2012/0287962 A1   Nov. 15, 2012

(30) Foreign Application Priority Data

May 9, 2011 (JP) ................................ 2011-104528

(51) Int. Cl.
G01N 25/22 (2006.01)
G01K 1/00 (2006.01)
G01K 17/00 (2006.01)

(52) U.S. Cl.
CPC .................................. *G01K 17/006* (2013.01)
USPC ............... 374/37; 374/148; 374/36; 374/147; 374/208

(58) Field of Classification Search
USPC ............................... 374/37, 36, 147, 208, 148
See application file for complete search history.

(56) References Cited

U.S. PATENT DOCUMENTS

| | | | |
|---|---|---|---|
| 4,059,982 A | 11/1977 | Bowman | |
| 4,956,793 A | 9/1990 | Bonne et al. | |
| 5,169,450 A * | 12/1992 | Opad et al. | 118/621 |
| 5,756,878 A | 5/1998 | Muto et al. | |
| 6,019,505 A | 2/2000 | Bonne et al. | |
| 6,517,237 B1 | 2/2003 | Hammond et al. | |
| 6,997,037 B2 | 2/2006 | Thurston | |
| 7,091,509 B2 | 8/2006 | Rahmouni et al. | |
| 7,926,323 B2 | 4/2011 | Ooishi et al. | |
| 8,005,293 B2 | 8/2011 | Kowalczyk et al. | |
| 2004/0261497 A1 | 12/2004 | Thurston et al. | |
| 2005/0034532 A1 | 2/2005 | Wible | |

(Continued)

FOREIGN PATENT DOCUMENTS

| | | |
|---|---|---|
| CN | 101421592 A | 4/2009 |
| CN | 101504384 A | 8/2009 |

(Continued)

OTHER PUBLICATIONS

A. J. Smola, et al., "A Tutorial on Support Vector Regression" (NeuroCOLT2 Technical Report Series NC-TR-1998-030), Oct. 1998.

(Continued)

*Primary Examiner* — Mirellys Jagan
(74) *Attorney, Agent, or Firm* — Troutman Sanders LLP

(57) ABSTRACT

A calorific value measuring system, includes a gas flowing in a pipe; the flow rate controlling device; a temperature measuring element in the pipe; a heater element, in the pipe, producing a plurality of temperatures; a measuring portion measuring a value from a temperature measuring element that is dependent on the temperature of the gas, and a value from the heater element at each of a plurality of temperatures; an equation storage device storing a calorific value equation using values from the temperature measuring element and values from the heater element at the plurality of temperatures as independent variables and uses the calorific value as the dependent variable; and a calorific value portion calculating a value for the calorific value of a gas through substituting a value from the temperature measuring element and a value from the heater element into the independent variables of the calorific value equation.

8 Claims, 20 Drawing Sheets

(56) References Cited

U.S. PATENT DOCUMENTS

| | | |
|---|---|---|
| 2005/0049805 A1 | 3/2005 | Bonne et al. |
| 2009/0193872 A1 | 8/2009 | Tokuda et al. |
| 2009/0277246 A1 | 11/2009 | Ooishi et al. |
| 2010/0294021 A1 | 11/2010 | Makino et al. |
| 2011/0185789 A1 | 8/2011 | Ooishi et al. |
| 2011/0257898 A1 | 10/2011 | Ooishi |

FOREIGN PATENT DOCUMENTS

| | | |
|---|---|---|
| EP | 0348244 A2 | 12/1989 |
| EP | 1947450 A1 | 7/2008 |
| EP | 2009431 A1 | 12/2008 |
| EP | 2345891 A | 7/2011 |
| EP | 2369337 A2 | 9/2011 |
| EP | 2369338 A2 | 9/2011 |
| EP | 2381248 A1 | 10/2011 |
| JP | H 3-53149 | 3/1991 |
| JP | 5-141999 A | 6/1993 |
| JP | H 8-50109 | 2/1996 |
| JP | 8-75688 | 3/1996 |
| JP | 2002-500357 | 1/2002 |
| JP | 2004-514138 A | 5/2004 |
| JP | 2007-248220 A | 9/2007 |
| JP | 2007-292730 A | 11/2007 |
| WO | 02/40992 A1 | 5/2002 |
| WO | WO 2007/037209 | 4/2007 |
| WO | WO 2010/038285 | 4/2010 |

OTHER PUBLICATIONS

Ulbig, Peter, et al. "Determination of the calorific value of natural gas by different methods", Thermochimica Acta, Elsevier Science Publishers, Amsterdam, NL, vol. 382, Jan. 2002, pp. 27-35, XP002639490.

Loubar, et al. "A combustionless determination method for combustion properties of natural gases", Fuel, IPC Science and Technology Press, Guildford, GB, vol. 86, No. 16, Oct. 2007, pp. 2535-2544, XP022293299.

Extended European Search Report, dated May 6, 2013, which issued during the prosecution of European Patent Application No. 08877144.9 (EP2345891).

Extended European Search Report, dated May 6, 2013, which issued during the prosecution of European Patent Application No. 11151331.3 (EP2369337).

Extended European Search Report, dated Apr. 5, 2012, which issued during the prosecution of European Patent Application No. 11159687.0 (EP2369338).

File History of Utility U.S. Appl. No. 13/090,602.

File History of Utility U.S. Appl. No. 13/121,765.

File History of Utility U.S. Appl. No. 13/739,039.

Extended European Search Report, dated Sep. 22, 2011, which issued during the prosecution of European Patent Application No. 11163139.6 (EP2381248).

H. Muto, et al., Netsudendoritsushiki Bunsekikei ni yoru Toshi Gas Hatsunetsuryo Sokutei (Thermal Conductivity Analyzer for City Gas Calorimeter), Savemation Rev, Feb. 1, 1995, vol. 13, No. 1, pp. 35-39.

N. V. Karlov, "Laser Action on Thermal Diffusion of Gases", 1982 Plenum Publishing Corporation, p. 231-239.

S. C. Saxena, "Transport Properties of Gases and Gaseous Mixtures at High Temperatures", Department 0/ Energy Engineering, University of Illinois at Chicago Circle, Chicago, Illinois 60680, Received Dec. 9, 1970, pp. 168-188, High Temperature Science 3, 168-188 (1971).

S. Udina et al: "A micromachined thermoelectric sensor for natural gas analysis: Thermal model and experimental results", Sensors and Actuators B, Elsevier Sequoia SA, Lausanne, CH, vol. 134, No. 2, Sep. 25, 2008, pp. 551-558, XP025429938.

Y. Ooishi, et al., Tennen Gas no Netsuryo Ryuryo Keisoku no Kanosei ni Tsuite (Calorific flow rate measurement of natural gases), Proceedings of Sensing Forum, 2005, vol. 22, pp. 371-375.

* cited by examiner

CALORIFIC VALUE MEASURING SYSTEM AND CALORIFIC VALUE MEASURING METHOD

CROSS REFERENCE TO RELATED APPLICATIONS

The present application claims priority under 35 U.S.C. §119 to Japanese Patent Application No. 2011-104528, filed May 9, 2011, which is incorporated herein by reference.

FIELD OF TECHNOLOGY

The present invention relates to a calorific value measuring system and calorific value measuring method relating to a gas testing technology.

BACKGROUND

Conventionally, it has been necessary to use costly gas chromatography equipment, or the like, to analyze the compliments of a mixed gas when calculating the amount of heat production of a mixed gas. Additionally, there have been proposals for a method for calculating the amount of heat production from a mixed gas by calculating the ratio of methane ($CH_4$), propane ($C_3H_8$), nitrogen ($N_2$), and carbon dioxide gas ($CO_2$) components included in the mixed gas through measuring the thermal conductivity of the mixed gas and the speed of sound in the mixed gas (See, for example, Japanese Examined Patent Application Publication 2004-514138 ("JP '138")).

However, the method disclosed in JP '138 requires a costly speed-of-sound sensor to measure the speed of sound, in addition to a sensor for measuring the thermal conductivity. Given this, one object of the present invention is the provision of a calorific value measuring system and calorific value measuring method whereby the calorific value of a gas can be measured easily.

SUMMARY

Examples of the present invention provides a calorific value measuring system, including (a) a pipe wherein a fluid flows; (b) flow rate controlling device for controlling a flow rate of the fluid that flows with in the pipe; (c) a temperature measuring element disposed within the pipe; (d) a heater element, disposed within the pipe, for producing heat at a plurality of heat producing temperatures; (e) a measuring portion for measuring a value for an electric signal from a temperature measuring element that is dependent on the temperature of the gas that is flowing within the pipe, and a value for an electric signal from a heater element at each of a plurality of heat producing temperatures; (f) an equation storage device for storing a calorific value calculating equation that uses an electric signal from the temperature measuring element and electric signals from the heater element at the plurality of heat producing temperatures as independent variables and uses the calorific value as the dependent variable; and (g) a calorific value calculating portion for calculating a value for the calorific value of a gas through substituting a value of an electrical signal from the temperature measuring element and a value of an electric signal from the heater element into an independent variable of an electric signal from a temperature measuring element and an independent variable of an electric signal from a heater element, in the calorific value calculating equation.

Examples of the present invention provides a method for measuring a calorific value, including: (a) a gas being caused to flow in the pipe; (b) the acquisition, from a temperature measuring element, of an electric signal that is dependent on the temperature of the gas flowing in the pipe; (c) the heater element that is in contact with the mixed gas that flows within the pipe being caused to produce heat at a plurality of heat producing temperatures; (d) the acquisition of a value for an electric signal from the heater element at each of the plurality of heat producing temperatures; (e) the preparation of a calorific value calculating equation that uses an electric signal from the temperature measuring element and electric signals from the heater element at the plurality of heat producing temperatures as independent variables and uses the calorific value as the dependent variable; and (f) the calculation of a value for the calorific value of a gas through substituting a value of an electrical signal from the temperature measuring element and a value of an electric signal from the heater element into the independent variable of an electric signal from a temperature measuring element and an independent variable of an electric signal from a heat-producing element in the calorific value calculating equation.

The examples of the present invention provide a calorific value measuring system, having (a) a pipe in which a gas is flowing; (b) the flow rate controlling device for controlling a flow rate of the gas that is flowing within the pipe; (c) a measuring portion for measuring a measured value of a gas radiation coefficient or a thermal conductivity of the gas that is flowing within the pipe; (d) a storage device for storing a correlation between a radiation coefficient or a thermal conductivity and a calorific value; (e) and a calorific value calculating portion for calculating a measured value for a calorific value of a gas based on a measured value for a radiation coefficient or thermal conductivity of the gas and the correlation.

The present invention enables the provision of a calorific value measuring system and a calorific value measuring method able to measure the calorific value of a gas easily and accurately.

DETAILED DESCRIPTION

Examples of the present invention are described below. In the descriptions of the drawings below, identical or similar components are indicated by identical or similar codes. Note that the diagrams are schematic. Consequently, specific measurements should be evaluated in light of the descriptions below. Furthermore, even within these drawings there may, of course, be portions having differing dimensional relationships and proportions.

Figure 1:
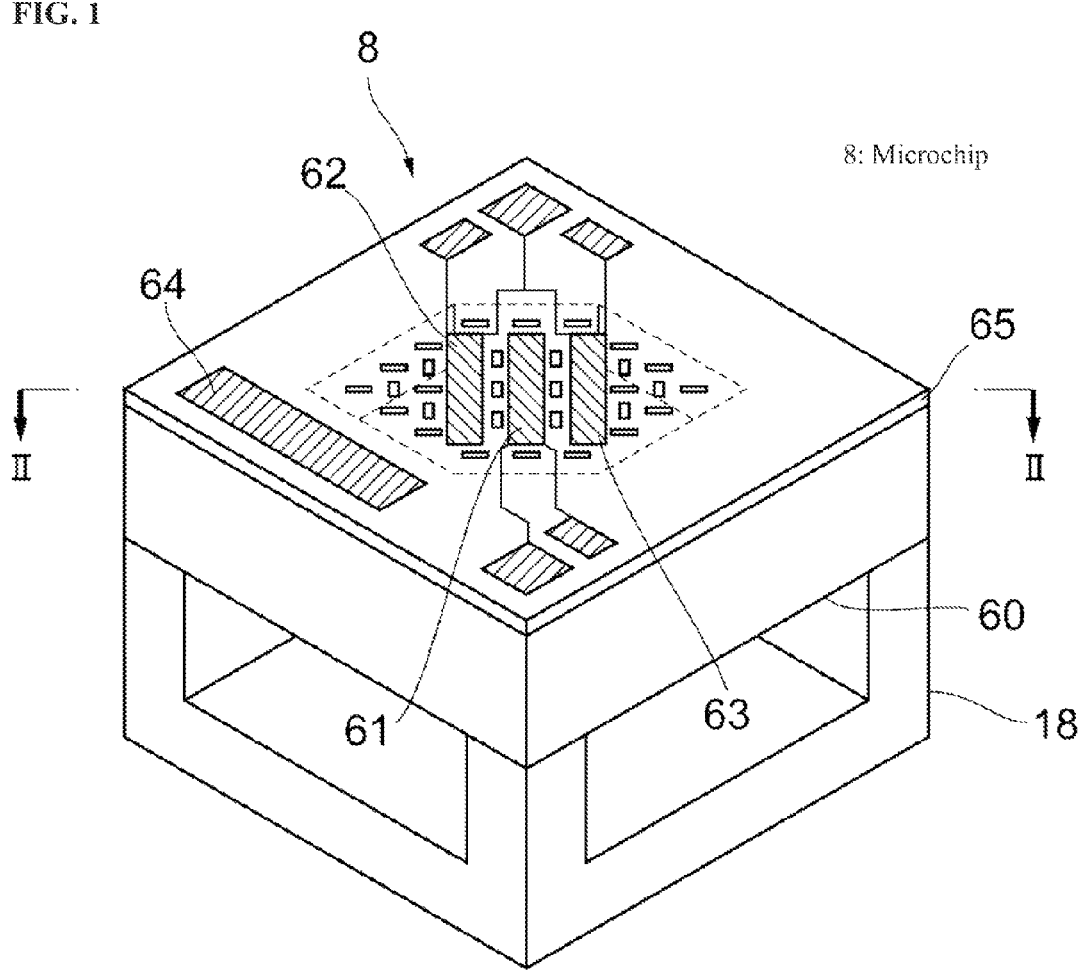
FIG. 1 is a perspective view of a first microchip as set forth in an example of the present invention.
Figure 2:
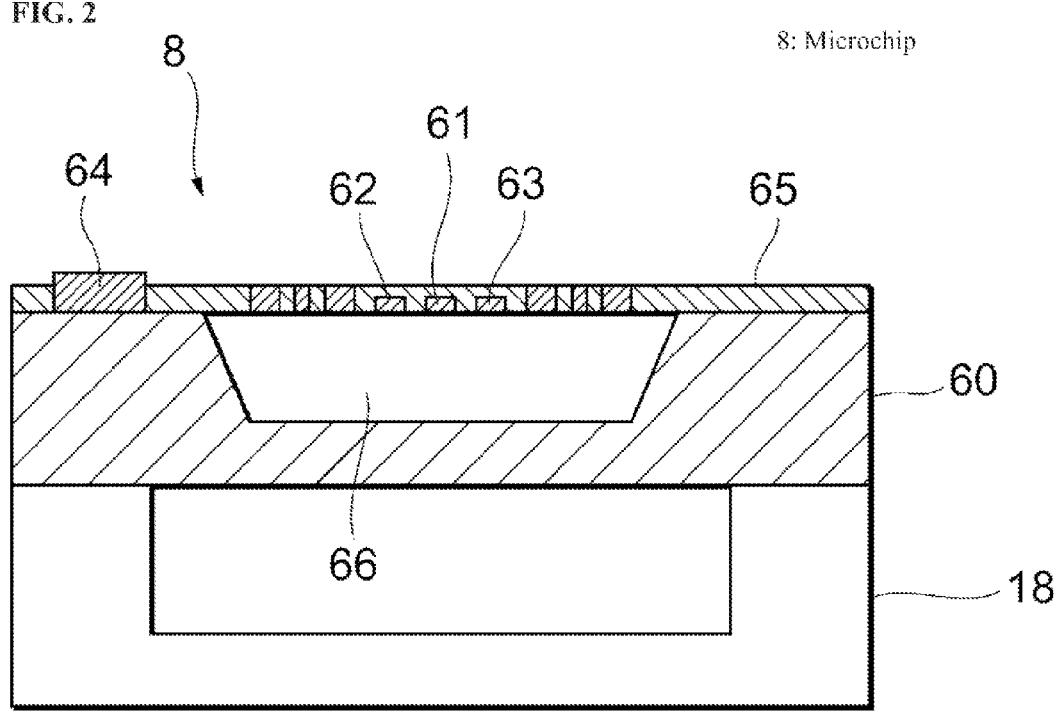
FIG. 2 is a cross-sectional diagram, viewed from the direction of the section II-II in FIG. 1, of the first microchip as set forth in another example of the present invention.

First a microchip 8 that is used in a calorific value measuring system is described in reference to FIG. 1, which is a perspective diagram, and FIG. 2, which is a cross-sectional diagram that is viewed from the direction of the section II-II. The microchip 8 includes a substrate 60, which is provided with a cavity 66, and a insulating layer 65, which is disposed so as to cover the cavity 66 on the substrate 60. The thickness of the substrate 60 is, for example, 0.5 mm. The length and width dimensions of the substrate 60 are, for example, 1.5 mm each. The portion of the insulating layer 65 that covers the cavity 66 forms a thermally insulating diaphragm. The microchip 8 further comprises a heater element 61 that is provided on a portion of the diaphragm of the insulating layer 65, a first temperature measuring element 62 and a second temperature measuring element 63 provided in a portion of the diaphragm of the insulating layer 65 so that the heater element 61 is interposed therebetween, and a temperature maintaining element 64 that is provided on the substrate 60.

Figure 3:
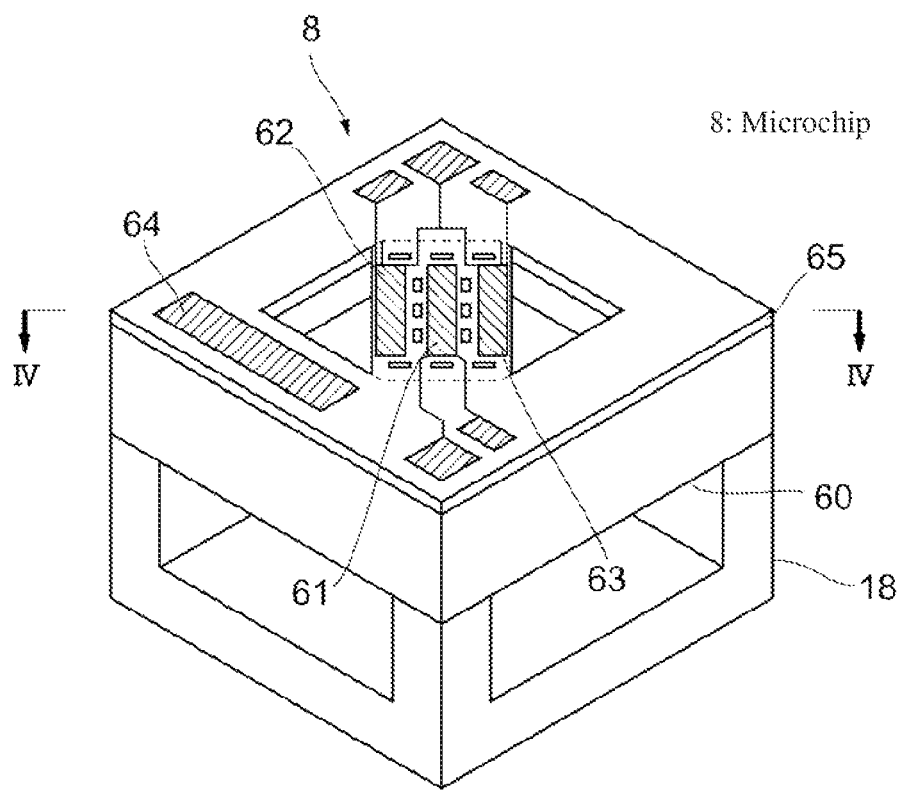
FIG. 3 is a perspective view of a second microchip as set forth in a further example.
Figure 4:
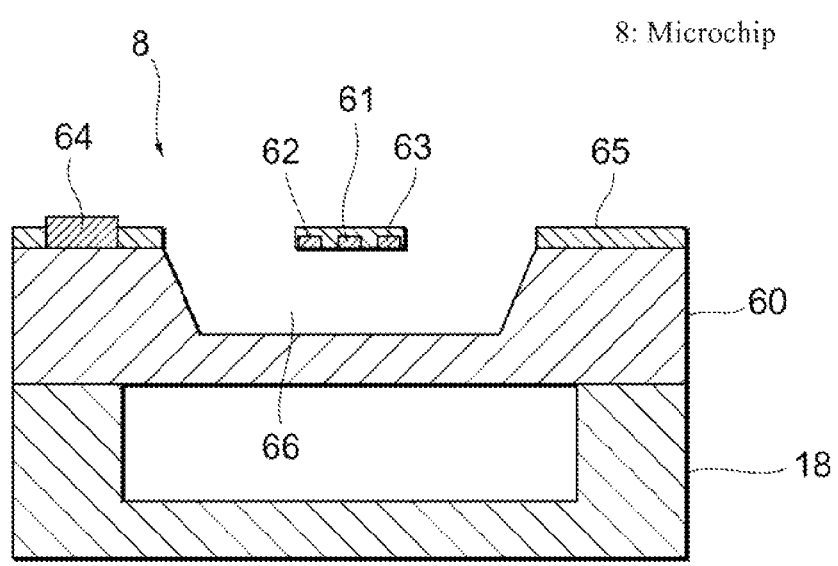
FIG. 4 is a cross-sectional diagram, viewed from the direction of the section IV-IV in FIG. 3, of the second microchip as set forth above.

A plurality of holes is provided in the diaphragm. The provision of the plurality of holes in the diaphragm expedites the exchange of gasses within the cavity 66. Conversely, the insulating layer 65, as illustrated in FIG. 3 and in FIG. 4, which is a cross-sectional diagram when viewed in the direction of the section IV-IV, may be disposed on the substrate 60 so as to cover the cavity 66 in the form of a bridge. This also exposes the inside of the cavity 66, expediting the exchange of gasses within the cavity 66.

The heater element 61 is disposed in the center of the portion of the diaphragm of the insulating layer 65 that covers the cavity 66. The heater element 61 is, for example, a resistor, and produces heat through the supply of electric power thereto, to heat the ambient gas that contacts the heater element 61. The first temperature measuring element 62 and the second temperature measuring element 63 are electrical elements that are, for example, passive elements such as resistors, and output electric signals that are dependent on the gas temperatures of the surrounding gases. An example of use of the output signal of the first temperature measuring element 62 will be explained below, but there is no limitation thereto, but rather, for example, an average value of the output signal from the first temperature measuring element 62 and the output signal of the second temperature measuring element 63 may be used as the output signal of the temperature measuring elements.

The temperature maintaining element 64 is, for example, a resistor, to which electricity is applied to produce heat, to maintain the substrate 60 at a constant temperature. Silicon (Si), or the like, may be used as the material for the substrate 60. Silicon dioxide ($SiO_2$), or the like, may be used as the material for the insulating layer 65. The cavity 66 may be formed through anisotropic etching, or the like. Furthermore, platinum (Pt) or the like may be used as the material for the first temperature measuring element 62, the second temperature measuring element 63, and the temperature maintaining element 64, and they may be formed through a lithographic method, or the like. Moreover, the heater element 61, the first temperature measuring element 62, and the second temperature measuring element 63 may be formed from the same member.

The microchip 8 is secured to a pipe, in which flows the ambient gas, through, for example, a thermally insulating member that is disposed on the bottom face of the microchip 8. Securing the microchip 8 through a thermally insulating member 18 within a pipe makes the temperature of the microchip 8 less susceptible to temperature variations of the inner wall of the pipe. The thermal conductivity of the insulating member 18, made from glass, or the like, is, for example, no more than 1.0 W/(m·K).

Figure 5:
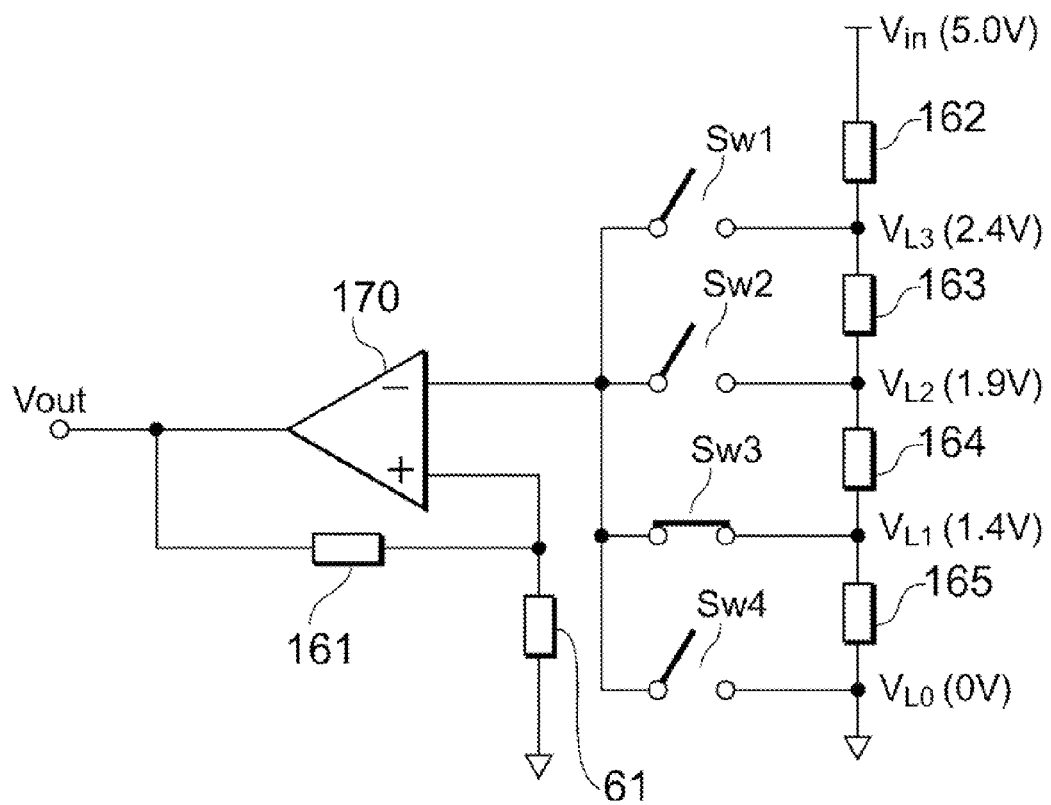
FIG. 5 is a circuit diagram relating to a heater element according to a et further example.

As illustrated in FIG. 5, one end of the heater element 61 is connected electrically to a + input terminal of an operational amplifier 170, for example, with the other end grounded. A resistive element 161 is connected, in parallel, to the + input terminal and the output terminal of the operational amplifier 170. The − input terminal of the operational amplifier 170 is connected electrically between a resistive element 162 and a resistive element 163, which are connected in series, between the resistive element 163 and a resistive element 164, which are connected in series, between the resistive element 164 and a resistive element 165, which are connected in series, or between the resistive element 165 and a ground terminal. The appropriate selection of the resistance values for each of the resistive elements 162 through 165 will produce a voltage VL3 of, for example, 2.4 V between the resistive element 163 and 162 when a voltage Yin of, for example, 5.0V is applied to one end of the resistive element 162. Additionally, a voltage $V_{L2}$ of, for example, 1.9 V is produced between the resistive element 164 and the resistive element 163, and a voltage $V_{L1}$ of for example, 1.4 V is produced between the resistive element 165 and the resistive element 164.

A switch SW1 is connected between the resistive element 162 and the resistive element 163 and the "−" input terminal of the operational amplifier 170, and a switch SW2 is connected between the resistive element 163 and the resistive element 164 and the "−" input terminal of the operational amplifier 170. Furthermore, a switch SW3 is provided between the resistive element 164 and the resistive element 165 and the "−" input terminal of the operational amplifier 170, and a switch SW4 is provided between the resistive element 165 and ground terminal and the "−" input terminal of the operational amplifier.

When applying the voltage $V_{L3}$ of 2.4 V to the − input terminal of the operational amplifier 170, only switch SW1 is turned ON, and switches SW2, SW3, and SW4 are turned OFF. When applying the voltage $V_{L2}$ of 1.9 V to the − input terminal of the operational amplifier 170, only switch SW2 is turned ON, and switches SW1, SW3, and SW4 are turned OFF. When applying the voltage $V_{L1}$ of 1.4 V to the − input terminal of the operational amplifier 170, only switch SW3 is turned ON, and switches SW1, SW2, and SW4 are turned OFF. When applying the voltage $V_{L4}$ of 1.4 V to the − input terminal of the operational amplifier 170, only switch SW3 is turned ON, and switches SW1, SW2, and SW4 are turned OFF. Consequently, 0V and any of three levels of voltages can be applied to the − input terminal of the operational amplifier 170 through turning the switches SW1, SW2, SW3, and SW4 ON and OFF. Because of this, the applied voltages, which determine the heat producing temperature of the heater element 61, can be set to three different levels through opening and closing the switches SW1, SW2, SW3, and SW4.

Here the temperature of the heater element 61 when the 1.4 V voltage VL1 is applied to the + input terminal of the operational amp defined as TH1. Additionally, the temperature of the heater element 61 when the 1.9 V voltage VL2 is applied to the input terminal of the operational amplifier 170 is defined as TH2, and the temperature of the heater element 61 when the 2.4 V voltage VL3 is applied to the + input terminal of the operational amplifier 170 is defined as $T_{H3}$.

Figure 6:
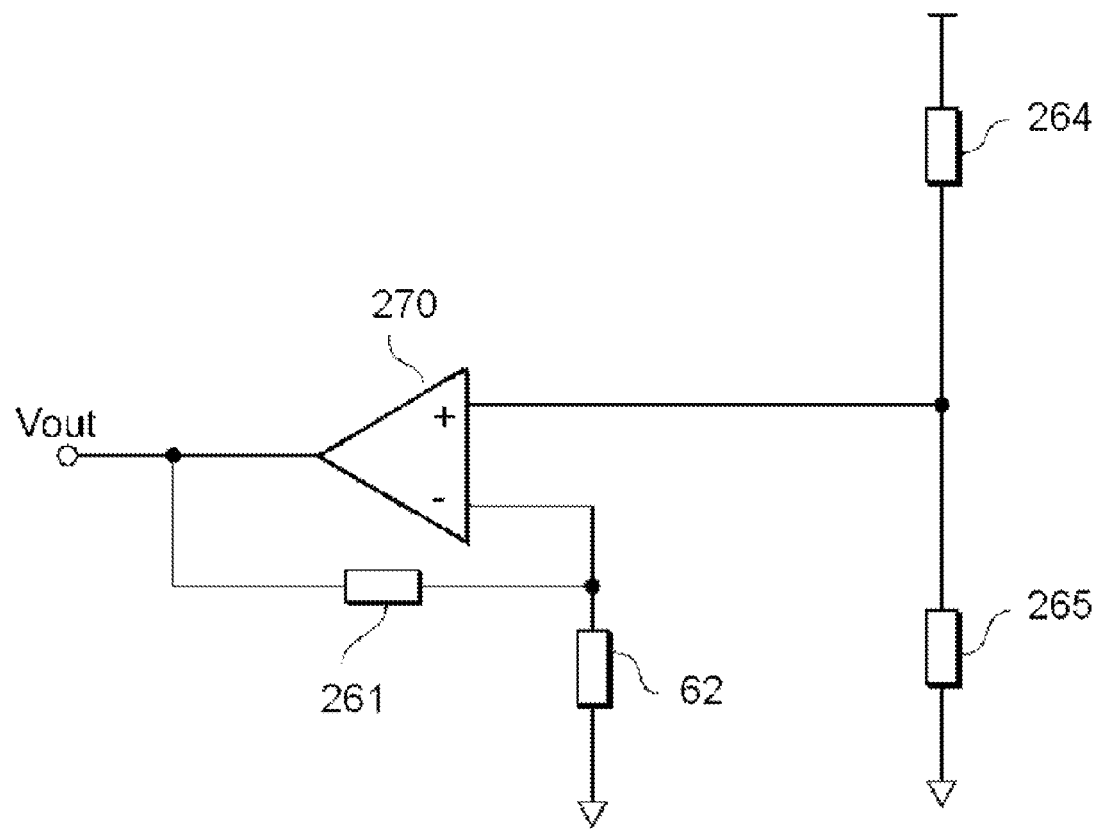
FIG. 6 is a circuit diagram relating to a temperature measuring element.

As illustrated in FIG. 6, one end of the first temperature measuring element 62 is connected electrically to a − input terminal of an operational amplifier 270, for example, with the other end grounded. A resistive element 261 is connected, in parallel, to the − input terminal and the output terminal of the operational amplifier 270. The + input terminal of the operational amplifier 270 is connected electrically to between a resistive element 264 and a resistive element 265 that are connected in series. This causes a weak voltage of about 0.3 V to be applied to the first temperature measuring element 62.

The resistance value of the heater element 61 illustrated in FIG. 1 and FIG. 2 varies depending on the temperature of the heater element 61. The relationship between the temperature $T_H$ of the heater element 61 and the resistance value $R_H$ of the heater element 61 is given through Equation (1), below:

$$R_H = R_{H\_STD} \times [1+\alpha_H(T_H - T_{H\_STD}) + \beta_H(T_H - T_{H\_STD})^2] \quad (1)$$

Here $T_{H\_STD}$ indicates a standard temperature for the heater element 61 of, for example, 20° C. $R_{H\_STD}$ indicates the resistance value of the heater element 61 measured in advance at the standards temperature of $T_{H\_STD}$. $\alpha_H$ indicates a first-order resistance temperature coefficient. $\beta_H$ indicates a second-order resistance temperature coefficient.

The resistance value $R_H$ of the heater element 61 is given by Equation (2), below, from the driving power $P_H$ of the heater element 61 and the current $I_H$ that flows through the heater element 61.

$$R_H = P_H / I_H^2 \quad (2)$$

Conversely, the resistance value $R_H$ of the heater element 61 is given by Equation (3), below, from the voltage $V_H$ applied to the heater element 61 and the current $I_H$ that flows through the heater element 61.

$$R_H = V_H / I_H \quad (3)$$

Here the temperature $T_H$ of the heater element 61 reaches a thermal equilibrium and stabilizes between the heater element 61 and the ambient gas. Note that this "thermal equilibrium" refers to a state wherein there is a balance between the heat production by the heater element 61 and the heat dissipation from the heater element 61 into the ambient gas. As shown in Equation (4), below, the driving power $P_H$ of the heater element 61 in the state of thermal equilibrium is divided by the difference $\Delta T_H$ between the temperature $T_H$ of the heat-producing element 61 and the temperature $T_I$ of the ambient gas; to produce the heat-dissipating factor $M_I$ of the ambient gas. Note that the units for the radiation coefficient $M_I$ are, for example, W/° C.

$$M_I = P_H / (T_H - T_I) = P_H / \Delta T_H \quad (4)$$

From Equation (1), above, the temperature $T_H$ of the heater element 61 is obtained through Equation (5), below:

$$T_H = (1/2\beta_H) \times [-\alpha_H + [\alpha_H^2 - 4\beta_H(1 - R_H/R_{H\_STD})]^{1/2}] + T_{H\_STD} \quad (5)$$

Consequently, the difference $\Delta T_H$ between the temperature $T_H$ of the heat-producing element 61 and the temperature $T_I$ of the ambient gas is given by Equation (6), below:

$$\Delta T_H = (1/2\beta_H) \times [-\alpha_H + [\alpha_H^2 - 4\beta_H(1 - R_H/R_{H\_STD})]^{1/2}] + T_{H\_STD} \quad (6)$$

The temperature $T_I$ of the ambient gas temperature $T_I$ is approximated by the temperature $T_I$ of the first temperature measuring element 62 when power is applied to the extent that it does not produce heat itself. The relationship between the temperature $T_I$ of the first temperature measuring element 62 and the resistance value $R_I$ of the first temperature measuring element 62 is given by Equation (7), below:

$$R_I = R_{I\_STD} \times [1 + \alpha_I(T_I - T_{I\_STD}) + \beta_I(T_I - T_{I\_STD})^2] \quad (7)$$

Here $T_{I\_STD}$ indicates a standard temperature for the first temperature measuring element 62 of, for example, 20° C. $R_{I\_STD}$ indicates the resistance value of the first temperature measuring element 62, measured in advance at the standard temperature of $T_{I\_STD}$. $A_1$ indicates a first-order resistance temperature coefficient. $B_1$ indicates a second-order resistance temperature coefficient. Through Equation (7), above, the temperature $T_I$ of the first temperature measuring element 62 is given by Equation (8), below:

$$T_I = (1/2\beta_I) \times [-\alpha_I + [\alpha_I^2 - 4\beta_I(1 - R_I/R_{I\_STD})]^{1/2}] + T_{I\_STD} \quad (8)$$

Consequently, the radiation coefficient $M_I$ of the ambient gas is given by Equation (9), below.

$$M_I = P_H / \Delta T_H = \quad (9)$$
$$P_H / \big[(1/2\beta_H)\big[-\alpha_H + [\alpha_H^2 - 4\beta_H(1 - R_H/R_{H\_STD})]^{1/2}\big] + T_{H\_STD} -$$
$$(1/2\beta_I)\big[-\alpha_I + [\alpha_I^2 - 4\beta_I(1 - R_I/R_{I\_STD})]^{1/2}\big] - T_{I\_STD}\big]$$

The electric current $I_H$ that flows in the heater element 61 and the driving power $P_H$ or the voltage $V_H$ can be measured, and thus the resistance value $R_H$ of the heater element 61 can be calculated from Equation (2) or Equation (3), above. Similarly, it is also possible to calculate the resistance value $R_I$ of the first temperature measuring element 62. Consequently, the radiation coefficient $M_I$ of the ambient gas can be calculated from Equation (9), above, using the microchip 8.

Note that holding the temperature of the substrate 60 constant, using the temperature maintaining element 64, causes the temperature of the ambient gas in the vicinity of the microchip 8, prior to heating by the heater element 61, to approximate the constant temperature of the substrate 60. This suppresses the variation in the temperature of the ambient gas prior to heating by the heater element 61. Further heating, by the heater element 61, the ambient gas for which the temperature variation had been controlled makes it possible to calculate the radiation coefficient $M_I$ with greater accuracy.

Here the ambient gas is a mixed gas, where the mixed gas is assumed to comprise four gas components: gas A, gas B, gas C, and gas D. The total of the volume fraction $V_A$ of the gas A, the volume fraction $V_B$ of the gas B, the volume fraction $V_C$ of the gas C, and the volume fraction $V_D$ of the gas D, as obtained by Equation (10), below, is 1.

$$V_A + V_B + V_C + V_D = 1 \quad (10)$$

Moreover, when the per-unit-volume calorific value of gas A is defined as $K_A$, the per-unit-volume calorific value of gas B is defined as $K_B$, the per-unit-volume calorific value of gas C is defined as $K_C$, and the per-unit-volume calorific value of gas D is defined as $K_D$, then the per-unit-volume calorific value Q of mixed gas is obtained by summing the products of the volume fractions of the individual gas components and the per-unit-volume calorific values of the individual gas components. Consequently, the per-unit-volume calorific value Q of the mixed gas is given by Equation (11), below. Note that the units for the per-unit-volume calorific values are, for example, MJ/m³.

$$Q = K_A \times V_A + K_B \times V_B + K_C \times V_C + K_D \times V_D \quad (11)$$

Moreover, when the radiation coefficient of gas A is defined as $M_A$, the radiation coefficient of gas B is defined as $M_B$, the radiation coefficient of gas C is defined as $M_C$, and the radiation coefficient of gas D is defined as $M_D$, then the radiation coefficient of the mixed gas $M_I$ is given by summing the products of the volume fractions of the individual gas components and the radiation coefficients of the individual gas components. Consequently, the radiation coefficient $M_I$ of the mixed gas is given by Equation (12), below.

$$M_I = M_A \times V_A + M_B \times V_B + M_C \times V_C + M_D \times V_D \quad (12)$$

Moreover, because the radiation coefficient of the gas is dependent on the temperature $T_H$ of the heater element 61, the radiation coefficient $M_I$ of the mixed gas is given by Equation (13) as a function of the temperature $T_H$ of the heater element 61:

$$M_I(T_H) = M_A(T_H) \times V_A + M_B(T_H) \times V_B + M_C(T_H) \times V_C + M_D(T_H) \times V_D \quad (13)$$

Consequently, when the temperature of the heater element 61 is $T_{H1}$, then the radiation coefficient $M_{I1}(T_{H1})$ of the mixed gas is given by Equation (14), below. Moreover, when the temperature of the heater element 61 is $T_{H2}$, then the radiation coefficient $M_{I2}(T_{H2})$ of the mixed gas is given by Equation (15), below, and when the temperature of the heater element 61 is $T_{H3}$, then the radiation coefficient $M_{I3}(T_{H3})$ of the mixed gas is given by Equation (16), below.

$$M_{I1}(T_{H1}) = M_A(T_{H1}) \times V_A + M_B(T_{H1}) \times V_B + M_C(T_{H1}) \times V_C + M_D(T_{H1}) \times V_D \quad (14)$$

$$M_{I2}(T_{H2}) = M_A(T_{H2}) \times V_A + M_B(T_{H2}) \times V_B + M_C(T_{H2}) \times V_C + M_D(T_{H2}) \times V_D \quad (15)$$

$$M_{I3}(T_{H3}) = M_A(T_{H3}) \times V_A + M_B(T_{H3}) \times V_B + M_C(T_{H3}) \times V_C + M_D(T_{H3}) \times V_D \quad (16)$$

If here the radiation coefficients $M_A(T_H)$, $M_B(T_H)$, $M_C(T_H)$, and $M_D(T_H)$ of the individual gas components are non-linear in respect to the temperature $T_H$ of the heater element 61, then the Equations (14) through (16), above, have linearly independent relationships. Moreover, even if the radiation coefficients $M_A(T_H)$, $M_B(T_H)$, $M_C(T_H)$, and $M_D(T_H)$ of the individual gas components are linear in respect to the temperature $T_H$ of the heater element 61, if the rates of change of the radiation coefficients $M_A(T_H)$, $M_B(T_H)$, $M_C(T_H)$, and $M_D(T_H)$ of the individual gas components are non-linear in respect to the temperature $T_H$ of the heater element 61 the Equations (14) through (16), above, have linearly independent relationships. Moreover, if Equations (14) through (16) have a linearly independent relationship, then Equation (10) and Equations (14) through (16) have a linearly independent relationship.

Figure 7:
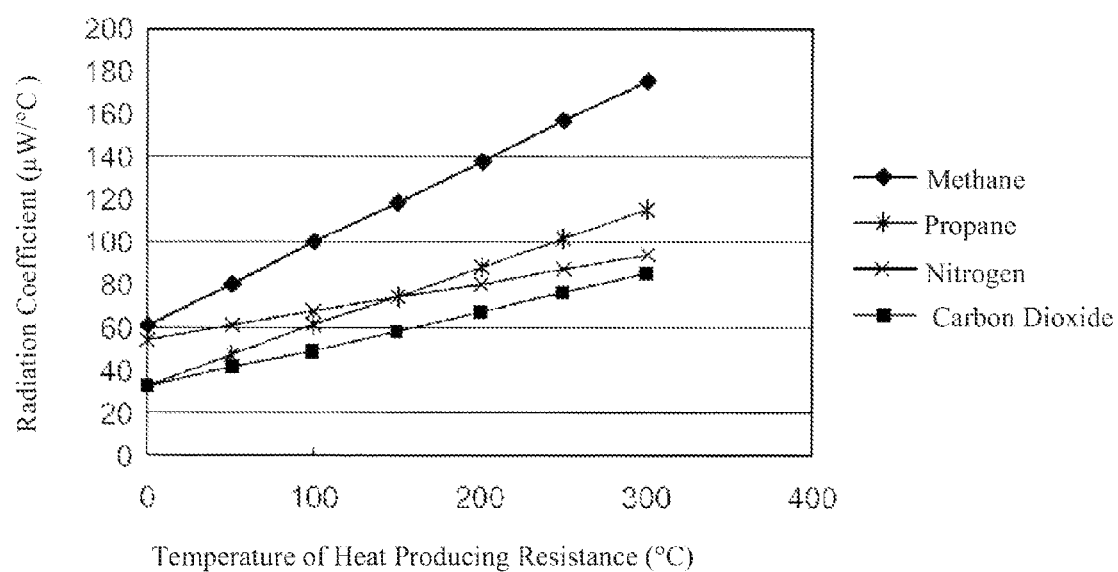
FIG. 7 is a graph illustrating the relationship between the temperature of the heater element and the radiation coefficient of the gas.

FIG. 7 is a graph showing the relationships of the radiation coefficients of methane ($CH_4$), propane ($C_3H_8$), nitrogen ($N_2$), and carbon dioxide ($CO_2$), which are included in natural gas, to the temperature of the heater element 61 which is a heat producing resistance. The radiation coefficients of each of these components (methane ($CH_4$), propane ($C_3H_8$), nitrogen ($N_2$), and carbon dioxide ($CO_2$)) are linear in respect to the temperature of the heater element 61. However, the respective rates of change of the radiation coefficients in respect to the temperature of the heater element 61 are different for methane ($CH_4$), propane ($C_3H_3$), nitrogen ($N_2$), and carbon dioxide ($CO_2$). Consequently, Equations (14) through (16), above, will be linearly independent if the gas components that comprise the mixed gas are methane ($CH_4$), propane ($C_3H_8$), nitrogen ($N_2$), and carbon dioxide ($CO_2$).

The values for the radiation coefficients $M_A(T_{H1})$, $M_B(T_{H1})$, $M_C(T_{H1})$, $M_D(T_{H1})$, $M_A(T_{H2})$, $M_B(T_{H2})$, $M_C(T_{H2})$, $M_D(T_{H2})$, $M_A(T_{H3})$, $M_B(T_{H3})$, $M_C(T_{H3})$, $M_D(T_{H3})$ for the individual gas components in Equation (14) through Equation (16) can be obtained in advance through measurements, or the like. Consequently, when the system of simultaneous equations of Equation (10) and Equation (14) through Equation (16) is solved, the volumetric fraction $V_A$ of the gas A, the volumetric fraction $V_B$ of the gas B, the volumetric fraction $V_C$ of the gas C, and the volumetric fraction $V_D$ of the gas D, respectively, are obtained as functions of the heat-dissipating factors $M_{I1}(T_{H1})$, $M_{I2}(T_{H2})$, and $M_{I3}(T_{H3})$ of the mixed gas. Note that in Equations (17) through (20), below, $f_n$, where n is a non-negative integer, is a code indicating a function:

$$V_A = f_1[M_{I1}(T_{H1}), M_{I2}(T_{H2}), M_{I3}(T_{H3})] \quad (17)$$

$$V_B = f_1[M_{I2}(T_{H1}), M_{I2}(T_{H2}), M_{I3}(T_{H3})] \quad (18)$$

$$V_C = f_3[M_{I1}(T_{H1}), M_{I2}(T_{H2}), M_{I3}(T_{H3})] \quad (19)$$

$$V_D = f_4[M_{I1}(T_{H1}), M_{I2}(T_{H2}), M_{I3}(T_{H3})] \quad (20)$$

Here Equation (21), below, is obtained through substituting Equation (17) through (20) into Equation (11), above.

$$Q = K_A \times V_A + K_B \times V_B + K_C \times V_C + K_D \times V_D = \quad (21)$$
$$KA \times f1[M_{I1}(T_{H1}), M_{I2}(T_{H2}), M_{I3}(T_{H3})] +$$
$$K_B \times f2[M_{I1}(T_{H1}), M_{I2}(T_{H2}), M_{I3}(T_{H3})] +$$

-continued $$KC \times f3[M_{I1}(T_{H1}), M_{I2}(T_{H2}), M_{I3}(T_{H3})] +$$
$$KD \times f4[M_{I1}(T_{H1}), M_{I2}(T_{H2}), M_{I3}(T_{H3})]$$

As shown in Equation (21), above, the per-unit-volume calorific value Q is obtained as an equation which has, as variables, the radiation coefficients $M_{I1}(T_{H1})$, $M_{I2}(T_{H2})$, and $M_{I3}(T_{H3})$ of the mixed gas when the temperatures of the heater element 61 are $T_{H1}$, $T_{H2}$, and $T_{H3}$. Consequently, the calorific value Q of the mixed gas is given by Equation (22), below, where g is a code indicating a function.

$$Q=g[M_{I1}(T_{H1}),M_{I2}(T_{H2}),M_{I3}(T_{H3})] \qquad (22)$$

Consequently, the inventors discovered that, for a mixed gas comprising a gas A, a gas B, a gas C, and a gas D, wherein the volume fraction $V_A$ of the gas A, the volume fraction $V_B$ of the gas B, the volume fraction $V_C$ of the gas C, and the volume fraction $V_D$ of the gas D, are unknown, it is possible to calculate easily the per-unit-volume calorific value of the mixed gas to be measured if Equation (22) is obtained in advance. Specifically, it is possible to calculate uniquely the calorific value Q of the mixed gas to be measured, through measuring the radiation coefficients $M_{I1}(T_{H1})$, $M_{I2}(T_{H2})$, and $M_{I3}(T_{H3})$ for the mixed gas to be measured, at the heat producing temperatures of $T_{H1}$, $T_{H2}$, and $T_{H3}$ of the heater element 61 and then substituting, into Equation (22).

Additionally, the radiation coefficient $M_I$ of the mixed gas, as indicated in Equation (9), above, depends on the resistance value $R_H$ of the heater element 61 and on the resistance value $R_I$ of the first temperature measuring element 62. Given this, the inventors discovered that the per-unit-volume calorific value Q of the thermal diffusion rate of a mixed gas can also be obtained from an equation having, as variables, the resistances $R_{H1}(T_{H1})$, $R_{H2}(T_{H2})$, and $R_{H3}(T_{H3})$ of the heater element 61 when the temperatures of the heater element 61 are $T_{H1}$, $T_{H2}$, and $T_{H3}$, and the resistance value $R_I$ of the first temperature measuring element 62 that is in contact with the mixed gas as shown in Equation (23), below, $$Q=g[R_{H1}(T_{H1}),R_{H2}(T_{H2}),R_{H3}(T_{H3}),Ri] \qquad (23)$$

Given this, the caloric content Q of a mixed gas to be measured can be calculated uniquely also by substituting, into Equation 23, the resistances $R_{H1}(T_{H1})$, $R_{H2}(T_{H2})$, and $R_{H3}(T_{H3})$ of the heater element 61 when the heat producing temperatures of the heater element 61, which is in contact with the mixed gas to be measured, are $T_{H1}$, $T_{H2}$, and $T_{H3}$, and the resistance value $R_I$ of the first temperature measuring element 62 that is in contact with the mixed gas.

Moreover, the per-unit-volume calorific value Q of the thermal diffusion rate of a mixed gas can also be Obtained from an equation having, as variables, the electric currents $I_{H1}(T_{H1})$, $I_{H2}(T_{H2})$, and $I_{H3}(T_{H3})$ in the heater element 61 when the temperatures of the heater element 61 are $T_{H1}$, $T_{H2}$, and $T_{H3}$, and the electric current of the first temperature measuring element 62 that is in contact with the mixed gas, as shown in Equation (24), below.

$$Q=g[I_{H1}(T_{H1}),I_{H2}(T_{H2}),I_{H3}(T_{H3}),I_I] \qquad (24)$$

Conversely, the per-unit-volume calorific value Q of the thermal diffusion rate of a mixed gas can also be obtained from an equation having, as variables, the voltages $I_{H1}(T_{H1})$, $I_{H2}(T_{H2})$, and $I_{H3}(T_{H3})$ applied to heater element 61 when the temperatures of the heater element 61 are $T_{H1}$, $T_{H2}$, and $T_{H3}$, and the voltage $V_I$ of the first temperature measuring element 62 that is in contact with the mixed gas, as shown in Equation (25), below.

$$Q=g[V_{H1}(T_{H1}),V_{H2}(T_{H2}),V_{H3}(T_{H3}),V_I] \qquad (25)$$

Conversely, the per-unit-volume calorific value of a mixed gas can also be obtained from an equation having, as variables, the output voltages $AD_{H1}(T_{H1})$, $AD_{H2}(T_{H2})$, and $AD_{H3}(T_{H3})$ of analog-digital converting circuits (hereinafter termed "A/D converting circuits") that are connected to the heater element 61 when the temperatures of the heater element 61 are $T_{H1}$, $T_{H2}$, and $T_{H3}$, and the output signal $AD_I$ of an A/D converting circuit that is connected to the first temperature measuring element 62 that is in contact with the mixed gas, as shown in Equation (26), below.

$$Q=g[AD_{H1}(T_{H1}),AD_{H2}(T_{H2}),AD_{H3}(T_{H3}),AD_I] \qquad (26)$$

Moreover, the per-unit-volume calorific value Q of the thermal diffusion rate of a mixed gas can also be obtained from an equation having, as variables, the electric signals $S_{H1}(T_{H1})$, $S_{H2}(T_{H2})$, and $S_{H3}(T_{H3})$ from the heater element 61 when the heat producing temperatures of the heater element 61 are $T_{H1}$, $T_{H2}$, and $T_{H3}$, and the electric signal $S_I$ of the first temperature measuring element 62 that is in contact with the mixed gas, as shown in Equation (27), below.

$$Q=g[S_{H1}(T_{H1}),S_{H2}(T_{H2}),S_{H3}(T_{H3}),S_I] \qquad (27)$$

Note that the gas components of the mixed gas are not limited to four different components.

For example, if the mixed gas comprises n types of gas components, then first a formula, given by Equation (28), below, is obtained using, as variables, the electric signals from the heater element 61 $S_{H1}(T_{H1})$, $S_{H2}(T_{H2})$, $S_{H3}(T_{H3})$, ..., $S_{Hn-1}(T_{Hn-1})$ at least n−1 different the heat producing temperatures $T_{H1}$, $T_{H2}$, $T_{H3}$, ..., $T_{Hn-1}$, and the electric signal $S_I$ from the first temperature measuring element 62. Given this, the per-unit-volume calorific value Q of the mixed gas to be measured can be calculated uniquely by measuring the values of the electric signals $S_{H1}(T_{H1})$, $S_{H2}(T_{H2})$, $S_{H3}(T_{H3})$, $S_{Hn-1}(T_{Hn-1})$ from the heater element 61, which contacts the mixed gas to be measured that comprises n different component gases for which the respective volume fractions are unknown, and the value of the electric signal $S_I$ from the first temperature measuring element 62, and then substituting into Equation (28).

$$Q=g[S_{H1}(T_{H1}),S_{H2}(T_{H2}),S_{H3}(T_{H3}),\ldots,S_{Hn-1}(T_{Hn-1}),S_I] \qquad (28)$$

Note that if the mixed gas includes an alkane ($C_jH_{2j+2}$) other than methane ($CH_4$) and propane ($C_3H_8$), where j is a natural number, in addition to methane ($CH_4$) and propane ($C_3H_8$), then the alkane ($C_jH_{2j+2}$) other than methane ($CH_4$) and propane ($C_3H_8$) will be seen as a mixture of methane ($CH_4$) and propane ($C_3H_8$), and there will be no effect on the calculation in Equation (28). For example, as indicated in Equations (29) through (32), below, the calculation may be performed using Equation (28) by viewing ethane ($C_2H_6$), butane ($C_4H_{10}$), pentane ($C_5H_{12}$), and hexane ($C_6H_{14}$) as a mixture of methane ($CH_4$) and propane ($C_3H_8$), with each multiplied by the respective specific factors.

$$C_2H_6=0.5CH_4+0.5C_3H_8 \qquad (29)$$

$$C_4H_{10}=-0.5CH_4+1.5C_3H_8 \qquad (30)$$

$$C_5H_{12}=-1.0CH_4+2.0C_3H_8 \qquad (31)$$

$$C_6H_{14}=-1.5CH_4+2.5C_3H_8 \qquad (32)$$

Consequently, with z as a natural number, if a mixed gas comprising n types of gas components includes, as gas components, z types of alkanes ($C_jH_{2j+2}$) other than methane ($CH_4$) and propane ($C_3H_8$), in addition to methane ($CH_4$) and propane ($C_3H_8$), an equation may be calculated having, as variables, the electric signals $S_H$ from the heater element 61 at, at least, n−z−1 different heat producing temperatures, and the electric signal $S_I$ from the first temperature measuring element 62.

Note that if the types of gas components in the mixed gas used in the calculation in Equation (28) are the same as the types of gas components of the mixed gas to be measured, wherein the per-unit-volume calorific value Q is unknown, then, of course, Equation (28) can be used in calculating the per-unit-volume calorific value Q of the mixed gas to be measured. Furthermore, Equation (28) can also be used when the mixed gas to be measured comprises a number of gas components that is less than n, where the gas components of the less than n different types are included in the mixed gas that was used for calculating Equation (28), if, for example, the mixed gas used in calculating Equation (28) included four types of gas components, namely methane ($CH_4$), propane ($C_3H_8$), nitrogen ($N_2$) and carbon dioxide ($CO_2$), then even if the mixed gas to be measured includes only three different components, namely methane ($CH_4$), propane ($C_3H_8$), and carbon dioxide ($CO_2$), without containing the nitrogen ($N_2$), still Equation (28) can be used in calculating the calorific value Q of the mixed gas to be measured.

Furthermore, if the mixed gas used in calculating Equation (28) included methane ($CH_4$) and propane ($C_3H_8$) as gas components, Equation (28) could still be used even when the mixed gas to be measured includes an alkane ($C_jH_{2j+2}$) that was not included in the mixed gas that was used in calculating Equation (28). This is because, as described above, even if the alkane ($C_jH_{2j+2}$) other than methane ($CH_4$) and propane ($C_3H_8$) is viewed as a mixture of methane ($CF_4$) and propane ($C_3H_8$) there is no effect on calculating the per-unit-volume calorific value Q using Equation (28).

Figure 8:
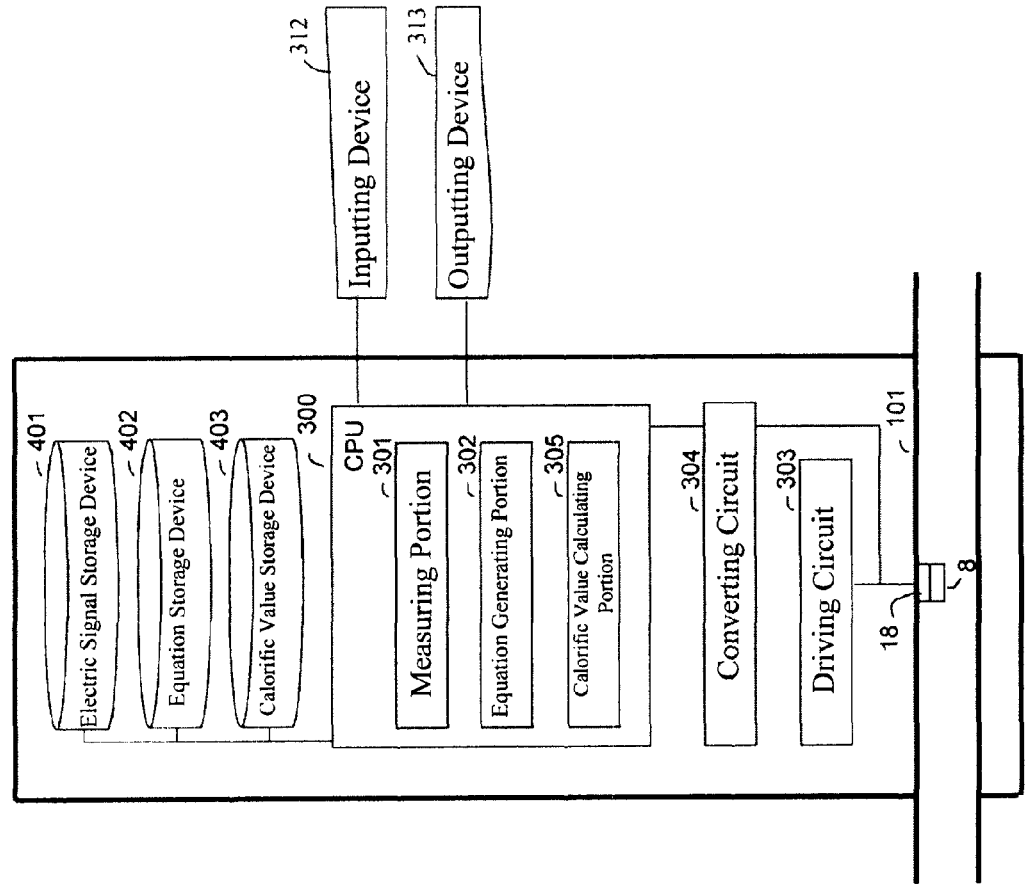
FIG. 8 is a first schematic diagram of a calorific value measuring system as set forth in an example according to the present invention.
Figure 9:
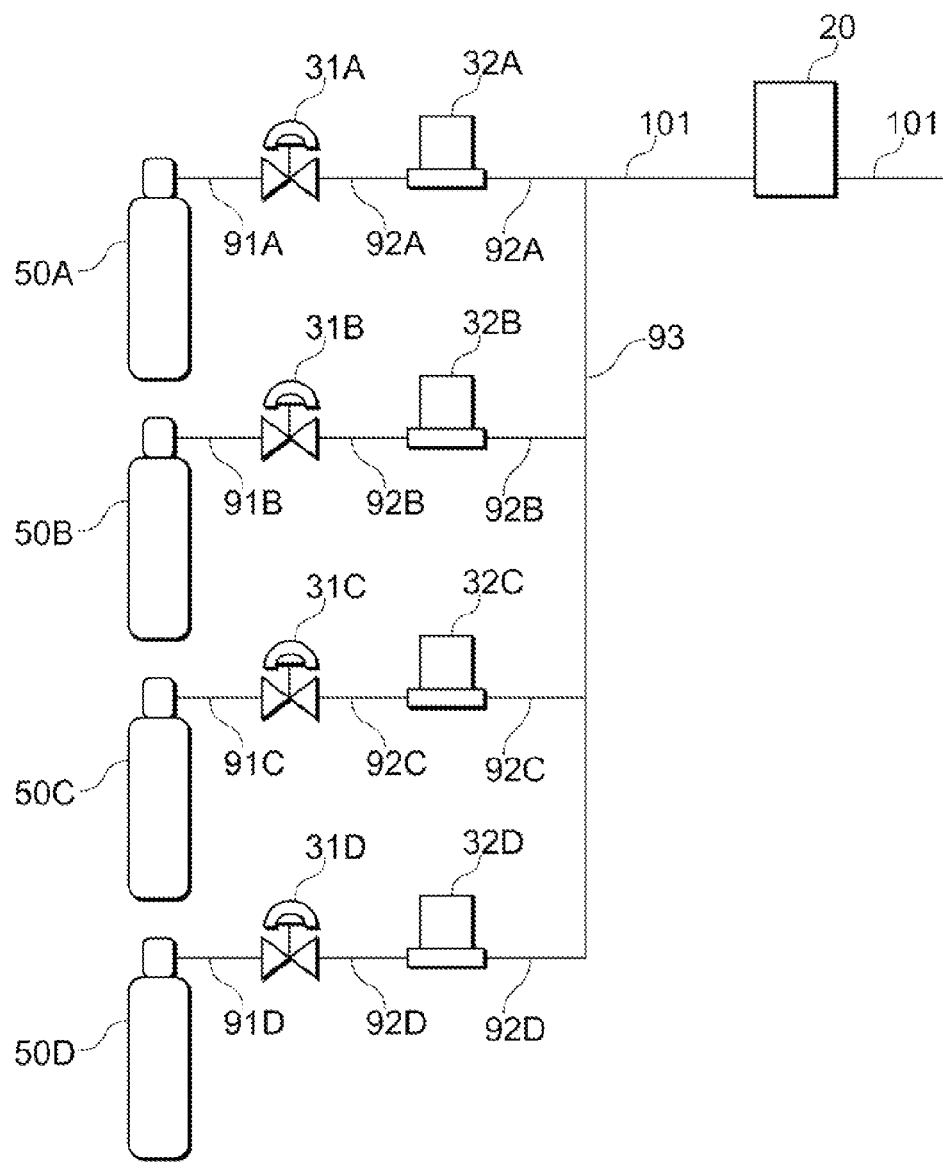
FIG. 9 is a second schematic diagram of a calorific value measuring system as set forth in an example.

Here the calorific value measuring system 20 according to the example illustrated in FIG. 8 and FIG. 9 includes a pipe 101 through which flow each of the plurality of sample mixed gases; and, disposed within the pipe 101, a microchip 8 that includes the first temperature measuring element 62 and the heater element 61 for producing heat at a plurality of heat producing temperatures $T_H$, illustrated in FIG. I, As illustrated in FIG. 8, the microchip 8 is disposed so as to protrude into the pipe 101, by means of a thermally insulating member 18. Note that the microchip 8 may be partially embedded in the side wall of the pipe 101, insofar as the first temperature measuring element 62 and the heater element 61, illustrated in FIG. 1 protrude into the pipe 101, as illustrated in FIG. 8. The arrangement of the microchip 8 so as to protrude into the pipe 101 expedites the replacement of the gas within the cavity 66 of the microchip 8, illustrated in FIG. 2, increasing the responsiveness of the microchip 8.

Figure 10:
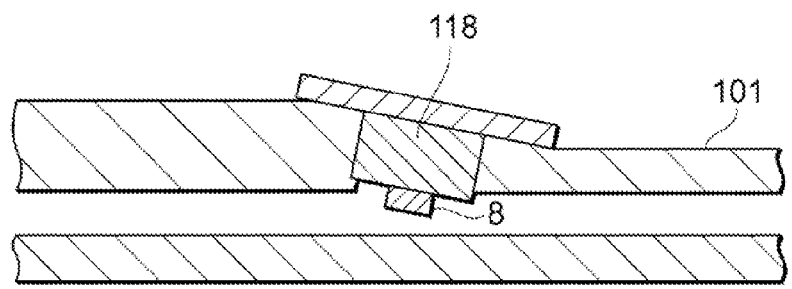
FIG. 10 is a first schematic diagram illustrating the arrangement of a microchip as set forth in a further example.
Figure 11:
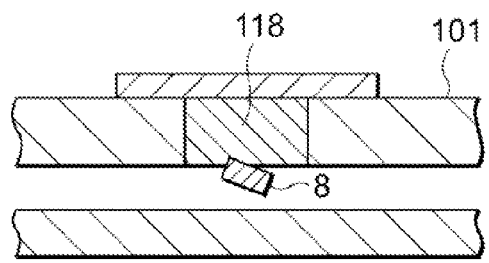
FIG. 11 is a second schematic diagram illustrating the arrangement of a microchip as set forth in a yet further example.

Moreover, as illustrated in FIG. 10, the microchip 8 may be disposed at an angle relative to the side watt of the pipe 101. In this case, as illustrated in FIG. 10, the package 118 as a whole, which includes the microchip 8 may be disposed at an angle relative to the side wall of the pipe 101, or, as illustrated in FIG. 11, the microchip 8 may be die-bonded at an angle relative to the package 118, to dispose the microchip 8 at an angle relative to the side wall of the pipe 101. The arrangement of the microchip 8 at an angle relative to the sidewall of the pipe 101 causes the microchip 8 to face the gas that flows with in the pipe 101, causing an efficient replacement of the gas within the cavity 66 of the microchip 8, illustrated in FIG. 2. The same is true for the microchip 8 illustrated in FIG. 4.

The calorific value measurement system 20 illustrated in FIG. 8 further includes a measuring portion 301, for measuring values of electric signals $S_I$ from the first temperature measuring element 62 that are dependent on the respective temperatures $T_I$ of the plurality of sample mixed gases, and the values of electric signals $S_H$ from the heater element 61 at each of the plurality of heat producing temperatures $T_H$; and equation generating portion 302 for generating a calorific value calculating equation based on known calorific values Q of a plurality of sample mixed gases, the values for the electric signals $S_I$ from the first temperature measuring element 62, and the plurality of values for the electric signals from the heater element 61 at the plurality of heat producing temperatures, having an electric signal $S_I$ from the first temperature measuring element 62 and the electric signals $S_H$ from the heater element 61 at the plurality of heat producing temperatures $T_H$ as independent variables, and having the calorific value Q as the dependent variable. Note that the sample mixed gasses include a plurality of types of gases.

When four types of sample mixed gases, each having a different calorific value Q, are used, then, as illustrated in FIG. 9, a first gas canister 50A for storing a first sample mixed gas, a second gas canister 50B for storing a second sample mixed gas, a third gas canister 50C for storing a third sample mixed gas, and a fourth gas canister 50D for storing a fourth sample mixed gas are prepared. The first gas canister 50A is connected, through a pipe 91A to a first gas pressure regulating device 31A for providing the first sample mixed gas from the first gas canister 50A, regulated to a low-pressure such as, for example, 0.2 MPa. Additionally, a first flow rate controlling device 32A is connected through a pipe 92A to the first gas pressure regulating device 31A. The first flow rate controlling device 32A controls the rate of flow of the first sample mixed gas that is fed into calorific value measuring system 20 through the pipes 92A and 101.

A second gas pressure regulating device 31B is connected through a pipe 91B to the second gas canister 50B. Additionally, a second flow rate controlling device 32B is connected through a pipe 92B to the second gas pressure regulating device 31B. The second flow rate controlling device 32B controls the rate of flow of the second sample mixed gas that is fed into calorific value measuring system 20 through the pipes 92B, 93, and 101.

A third gas pressure regulating device 31C is connected through a pipe 91C to the third gas canister 50C. Additionally, a third flow rate controlling device 32C is connected through a pipe 92C to the third gas pressure regulating device 31C. The third flow rate controlling device 32C controls the rate of flow of the third sample mixed gas that is fed into calorific value measuring system 20 through the pipes 92C, 93, and 101.

A fourth gas pressure regulating device $31_D$ is connected through a pipe 91D to the fourth gas canister 50D. Additionally, a fourth flow rate controlling device 32D is connected through a pipe 92D to the fourth gas pressure regulating device 31D. The fourth flow rate controlling device 32D controls the rate of flow of the fourth sample mixed gas that is fed into calorific value measuring system 20 through the pipes 92D, 93, and 101.

The first through fourth at sample mixed gases are each, for example, natural gas. The first through fourth sample mixed gases each include four different gas components of, for example, methane ($CH_4$), propane ($C_3H_8$), nitrogen ($N_2$), and carbon dioxide ($CO_2$).

When a first sample mixed gas flows, without stopping, in the pipe 101, illustrated in FIG. 8, the first temperature measuring element 62 of the microchip 8, illustrated in FIG. 1 and FIG. 2, outputs an electric signal $S_I$ that is dependent on the temperature of the first sample mixed gas. Following this, the heater element 61 applies driving powers $P_{H1}$, $P_{H2}$, and $P_{H3}$ from the driving circuit 303 illustrated in FIG. 8. When the driving powers $P_{H1}$, $P_{H2}$, and $P_{H3}$ are applied, the heater element 61 that is in contact with the first sample mixed gas, which is flowing, without stopping, within the pipe 101, produces heat at a temperature $T_{H1}$ of 100° C., a temperature $T_{H2}$ of 150° C. and a temperature $T_{H3}$ of 200° C., for example, to output an electric signal $S_{H1}$ ($T_{H1}$) at the heat producing temperature $T_{H1}$, an electric signal $S_{H2}$ ($T_{H2}$) at the heat producing temperature $T_{H2}$, and an electric signal $S_{H3}$ ($T_{H3}$) at the heat producing temperature $T_{H3}$.

After the removal of the first sample mixed gas from the pipe 101, the second through fourth sample mixed gases flow sequentially through the pipe 101. When the second sample mixed gas flows, without stopping, in the pipe 101, the first temperature measuring element 62 of the microchip 8, illustrated in FIG. 1 and FIG. 2, outputs an electric signal SI that is dependent on the temperature of the second sample mixed gas. The heater element 61, which is in contact with the second sample mixed gas that is flowing without stopping, outputs an electric signal $S_{H1}$ ($T_{H1}$) at a heat producing temperature $T_{H1}$, an electric signal $S_{H2}$ ($T_{H2}$) at a heat producing temperature $T_{H2}$, and an electric signal $S_{H3}$ ($T_{H3}$) at a heat producing temperature $T_{H3}$.

When a third sample mixed gas flows, without stopping, in the pipe 101, illustrated in FIG. 8, the first temperature measuring element 62 of the microchip 8, illustrated in FIG. 1 and FIG. 2, outputs an electric signal $S_I$ that is dependent on the temperature of the third sample mixed gas. The heater element 61, which is in contact with the third sample mixed gas that is flowing without stopping, outputs an electric signal $S_{H1}$ ($T_{H1}$) at a heat producing temperature $T_{H1}$, an electric signal $S_{H2}$ ($T_{H2}$) at a heat producing temperature $T_{H2}$, and an electric signal $S_{H3}$ ($T_{H3}$) at a heat producing temperature $T_{H3}$.

When a fourth sample mixed gas flows, without stopping, in the pipe 101, illustrated in FIG. 8, the first temperature measuring element 62 of the microchip 8, illustrated in FIG. 1 and FIG. 2, outputs an electric signal $S_I$ that is dependent on the temperature of the fourth sample mixed gas. The heater element 61, which is in contact with the fourth sample mixed gas that is flowing without stopping, outputs an electric signal. $S_{H1}$ ($T_{H1}$) at a heat producing temperature $T_{H1}$, an electric signal $S_{H2}$ ($T_{H2}$) at a heat producing temperature $T_{H2}$, and an electric signal $S_{H3}$ ($T_{H3}$) at a heat producing temperature $T_{H3}$.

Note that if there are n types of gas components in each of the sample mixed gases, the heater element 61 of the microchip 8, illustrated in FIG. 1 and FIG. 2, is caused to produce heat at at least n−1 different temperatures. However, as described above, an alkane ($C_jH_{2j+2}$) other than methane ($CH_4$) and propane ($C_3H_8$) can be viewed as a mixture of methane ($CH_4$) and propane ($C_3H_8$). Consequently, with z as a natural number, if a sample mixed gas comprising n types of gas components includes, as gas components, z types of alkanes ($C_jH_{2j+2}$) in addition to methane ($CH_4$) and propane ($C_3H_8$), the heater element 61 is caused to produce heat at n−z−1 different temperatures.

As illustrated in FIG. 8, the microchip 8 is connected to a central calculation processing device (CPU) 300 that includes the measuring portion 301. An electric signal storage device 401 is also connected to the CPU 300. The measuring portion 301 measures the value of the electric signal $S_I$ from the first temperature measuring element 62, and, from the heater element 61, the values of the electric signal $S_{H1}$ ($T_{H1}$) at the heat producing temperature $T_{H1}$, the electric signal $S_{H2}$ ($T_{H2}$) at the heat producing temperature $T_{H2}$, and the electric signal $S_{H3}$ ($T_{H3}$) at the heat producing temperature $T_{H3}$, and stores the measured values in the electric signal storage device 401.

Note that electric signal $S_I$ from the first temperature measuring element 62 may be the resistance value $R_I$ of the first temperature measuring element 62, the current $I_I$ flowing in the first temperature measuring element 62, the voltage $V_I$ applied to the first temperature measuring element 62, or the output signal $AD_I$ from the A/D converting circuit 304 that is connected to the first temperature measuring element 62. Similarly, the electric signal $S_H$ from the heater element 61 may be the resistance value $R_H$ of the heater element 61, the current $I_H$ flowing in the heater element 61, the voltage $V_H$ applied to the heater element 61, or the output signal $AD_H$ from the A/D converting circuit 304 that is connected to the heater element 61.

The equation generating portion 302 that is included in the CPU 300 collects the respective known values for the calorific values Q of, for example, each of the first through fourth sample mixed gases, the plurality of measured values for the electric signals $S_I$ from the first temperature measuring element 62, and the plurality of measured values for the electric signals $S_{H1}$ ($T_{H1}$), $S_{H2}$ ($T_{H2}$), and $S_{H3}$ ($T_{H3}$) from the heater element 61. Moreover, the equation generating portion 302 calculates a calorific value calculating equation, through multivariate statistics, based on the collected values for the calorific values Q, electric signals $S_I$, and electric signals $S_H$, with the electric signal $S_I$ from the first temperature measuring element 62, and the electric signals $S_{H1}(T_{H1})$, $S_{H2}(T_{H2})$, and $S_{H3}(T_{H3})$ from the heater element 61 as the independent variables and the calorific value Q as the dependent variable.

Note that "multivariate statistics" includes support vector analysis disclosed in A. J. Smola and B. Scholkopf (eds.), "A Tutorial on Support Vector Regression" (NeuroCOLT Technical Report NC-TR-98-030), multiple linear regression analysis, the Fuzzy Quantification Theory Type II, disclosed in Japanese Unexamined Patent Application Publication H5-141999, and the like.

The calorific value measuring system 20 is further provided with an equation storage device 402, connected to the CPU 300. The equation storage device 402 stores the calorific value calculating equation generated by the equation generating portion 302. An inputting device 312 and an outputting device 313 are also connected to the CPU 300. A keyboard, a pointing device such as a mouse, or the like, may be used as the inputting device 312. An image displaying device such as a liquid crystal display or a monitor, or a printer, or the like, may be used as the outputting device 313.

Figure 12:
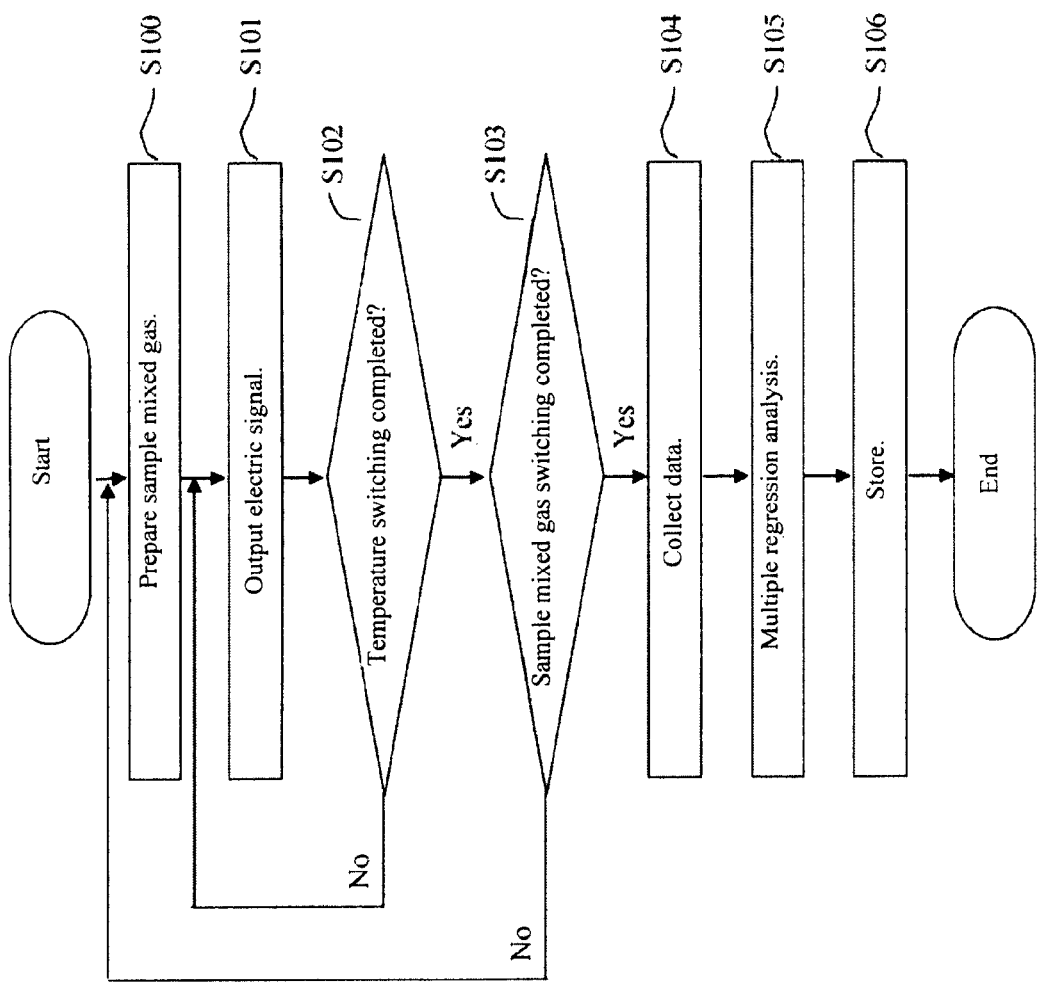
FIG. 12 is a flowchart illustrating a method for generating a calorific value calculating equation as set forth in examples according to the present invention.

The flowchart in FIG. 12 will be used next to explain a method for generating a calorific value calculating equation as set forth in an example.

(a) In Step S100, the valve for the first flow rate controlling device 32A is opened while leaving the second through fourth flow rate controlling devices 32B through 32D, illustrated in FIG. 9, closed, to introduce the first sample mixed gas into the pipe 101 illustrated in FIG. 8, in Step S101, the measuring portion 301 measures the value of the electric signal $S_I$ from the first temperature measuring element 62 that is in contact with the first sample mixed gas that flows without stopping within the pipe 101, and stores it in the electric signal storage device 401. Following this, the driving circuit 203 applies a driving power $P_{H1}$ to the heater element 61 illustrated in FIG. 1 and FIG. 2, to cause the heater element 61 produce heat at 100° C. The measuring portion 301, illustrated in FIG. 8, stores, into the electric signal storage device 401, the value of the electric signal $S_{H1}$ ($T_{H1}$) from the heater element 61 that produces heat at 100° C.

(b) In Step S102, the driving circuit 303 evaluates whether or not the switching of the temperatures of the heater element 61, illustrated in FIG. 1 and FIG. 2, has been completed. If the switching to the temperature of 150° C. and to the temperature of 200° C. has not been completed, then processing returns to Step S101, and the driving circuit 303, illustrated in FIG. 8, causes the heater element 61, illustrated in FIG. 1 and FIG. 2, to produce heat at 1150° C. The measuring portion 301, illustrated in FIG. 8, stores, into the electric signal storage device 401, the value of the electric signal $S_{H2}$ ($T_{H2}$) from the heater element 61 that is in contact with the first sample mixed gas that flows without stopping within the pipe 101 and that produces heat at 150° C.

(c) In Step S102, whether or not the switching of the temperatures of the heater element 61, illustrated in FIG. 1 and FIG. 2, has been completed is evaluated again. If the switching to the temperature of 200° C. has not been completed, then processing returns to Step S101, and the driving circuit 303, illustrated in FIG. 8, causes the heater element 61, illustrated in FIG. 1 and FIG. 2, to produce heat at 200° C. The measuring portion 301, illustrated in FIG. 8, stores, into the electric signal storage device 401, the value of the electric signal $S_{H3}$ ($T_{H3}$) from the heater element 61 that is in contact with the first sample mixed gas that flows without stopping within the pipe 101 and that produces heat at 200° C.

(d) If the switching of the temperature of the heater element 61 has been completed, then processing advances from Step S102 to Step S103. In Step S103, an evaluation is performed as to whether or not the switching of the sample mixed gases has been completed. If the switching to the second through fourth sample mixed gases has not been completed, processing returns to Step S100. In Step S100, the valve for the first flow rate controlling device 32A is closed and the valve for the second flow rate controlling device 32B is opened while leaving the third and fourth flow rate controlling devices 32C through 32D, illustrated in FIG. 9, closed, to introduce the second sample mixed gas into the pipe 101 illustrated in FIG. 8.

(e) The loop of Step S101 through Step S102 is repeated in the same manner as for the first sample mixed gas. The measuring portion 301 measures the value of the electric signal $S_I$ from the first temperature measuring element 62 that is in contact with the second sample mixed gas that flows without stopping within the pipe 101, and stores it in the electric signal storage device 401. Moreover, the measuring portion 301 stores, into the electric signal storage device 401, the values of the electric signals $S_{H1}$ ($T_{H1}$), $S_{H2}$ ($T_{H2}$), and $S_{H3}$ ($T_{H3}$) from the heater element 61 that is in contact with the second sample mixed gas that flows without stopping within the pipe 101 and that produces heat at 100° C., 150° C., and 200"C.

(f) Thereafter, the loop of Step S100 through Step S103 is repeated. Through this, the value of the electric signal $S_I$ from the first temperature measuring element 62 that is in contact with the third sample mixed gas that flows without stopping within the pipe 101, and the values of the electric signals $S_{H1}$ ($T_{H1}$), $S_{H2}$ ($T_{H2}$), and $S_{H3}$ ($T_{H3}$) from the heater element 61 that is in contact with the third sample mixed gas that flows without stopping within the pipe 101 and that produces heat at 100° C., 150° C., and 200° C. are stored into the electric signal storage device 401. Moreover, the value of the electric signal $S_I$ from the first temperature measuring element 62 that is in contact with the fourth sample mixed gas that flows without stopping within the pipe 101, and the values of the electric signals $S_{H1}$($T_{H1}$), $S_{H2}$ ($T_{H2}$), and $S_{H3}$ ($T_{H3}$) from the heater element 61 that is in contact with the fourth sample mixed gas that flows without stopping within the pipe 101 and that produces heat at 100° C., 150° C., and 200° C. are stored into the electric signal storage device 401.

(g) In Step) S104, the value for the known calorific value Q of the first sample mixed gas, the value for the known calorific value Q of the second sample mixed gas, the value for the known calorific value Q of the third sample mixed gas, and the value for the known calorific value Q of the fourth sample mixed gas are inputted into the equation generating portion 302 from the inputting device 312. Moreover, the equation generating portion 302 reads out, from the electric signal storage device 401, the plurality of measured values for the electric signal $S_I$ from the first temperature measuring element 62, and the plurality of measured values for the electric signals $S_{H1}$($T_{H1}$), $S_{H2}$($T_{H2}$), and $S_{H3}$($T_{H3}$) from the heater element 61.

(h) In Step S105, the equation generating portion 302 performs multiple linear regression analysis based on the values for the calorific values Q of the first through fourth sample mixed gases, the plurality of measured values for the electric signals $S_I$ from the first temperature measuring element 62, and the plurality of measured values for the electric signals $S_{H1}$ ($T_{H1}$), $S_{H2}$ ($T_{H2}$), and $S_{H3}$ ($T_{H3}$) from the heater element 61. Through the multiple linear regression analysis, the equation generating portion 302 calculates a calorific value calculating equation having the electric signal $S_I$ from the first temperature measuring element 62 and the electric signals $S_{H1}$($T_{H1}$), $S_{H2}$($T_{H2}$), and $S_{H3}$($T_{H3}$) from the heater element 61 as the independent variables and the calorific value Q of the gas as the dependent variable. Thereafter, in Step S106, the equation generating portion 302 stores, into the equation storage device 402, the equation that has been generated, to complete the method for generating the calorific value calculating equation as set forth in the example.

As described above, the method for generating a calorific value calculating equation as set forth in the example enables the generation of a calorific value calculating equation that calculates a unique value for the calorific value Q of a mixed gas being measured.

The functions of a calorific value measuring system 20 when measuring the calorific value Q of a mixed gas wherein calorific value Q is unknown is explained next. For example, a mixed gas to be measured, such as a natural gas that includes, at unknown volume fractions, methane ($CH_4$), propane ($C_3H_8$), nitrogen ($N_2$), and carbon dioxide gas ($CO_2$), with an unknown calorific value Q, is introduced into the pipe 101. The first temperature measuring element 62 of the microchip 8 illustrated in FIG. 1 and FIG. 2 outputs an electric signal $S_I$ that is dependent on the temperature of the gas that is measured, which is flowing without stopping within the pipe 101. Following this, the heater element 61 applies driving powers $P_{H1}$, $P_{H2}$, and $P_{H3}$ from the driving circuit 303 illustrated in FIG. 8. When the driving powers $P_{H1}$, $P_{H2}$, and $P_{H3}$ are applied, the heater element 61 that is in contact with the mixed gas to be measured, which is flowing, without stopping, within the pipe 101, produces heat at a temperature $T_{H1}$ of 100° C., a temperature $T_{H2}$ of 150° C., and a temperature $T_{H3}$ of 200° C., for example, to output an electric signal $S_{H1}$ ($T_{H1}$) at the heat producing temperature $T_{H1}$, an electric signal $S_{H2}$ ($T_{H2}$) at the heat producing temperature $T_{H2}$, and an electric signal $S_{H3}$ ($T_{H3}$) at the heat producing temperature $T_{H3}$.

The measuring portion 301, illustrated in FIG. 8, measures the values of the electric signal $S_I$, from the first temperature measuring element 62, which is dependent on the temperature $T_I$ of the mixed gas to be measured, which is in contact with the mixed gas to be measured, which is flowing without stopping within the pipe 101, and of the electric signal $S_{H1}$ ($T_{H1}$) at the heat producing temperature $T_{H1}$, the electric signal $S_{H2}$($T_{H2}$) at the heat producing temperature $T_{H2}$, and the electric signal $S_{H3}(T_{H3})$ at the heat producing temperature $T_{H3}$, from the heater element 61 that is in contact with the mixed gas to be measured, and stores the measured values into the electric signal storage device 401.

As described above, the equation storage device 402 stores a calorific value calculating equation that has, as independent variables, the electric signal $S_I$ from the first temperature measuring element 62, the electric signal $S_{H1}(T_{H1})$ from the heater element 61 with a heat producing temperature $T_{H1}$ of 100° C., the electric signal $S_{H2}(T_{H2})$ from the heater element 61 with a heat producing temperature $T_{H2}$ of 150° C., and the electric signal $S_{H3}(T_{H3})$ from the heater element 61 with a heat producing temperature $T_{H3}$ of 200° C., and that has, as the dependent variable, the calorific value Q of the gas.

The calorific value measuring system 20 according to the example further has a calorific value calculating portion 305. The calorific value calculating portion 305 substitutes the measured value for the electric value $S_I$ from the first temperature measuring element 62, and the measured values for the electric signals $S_{H1}(T_{H1})$, $S_{H2}(T_{H2})$, and $S_{H3}(T_{H3})$ from the heater element 61, respectively, into the independent variable for the electric value $S_I$ from the first temperature measuring element 62, and the independent variables for the electric signals $S_{H1}(T_{H1})$, $S_{H2}(T_{H2})$, and $S_{H3}(T_{H3})$ from the heater element 61, to calculate the measured value for the calorific value Q of the mixed gas to be measured, which flows without stopping within the pipe 101. A calorific value storage device 403 is also connected to the CPU 300. The calorific value storage device 403 stores the value for the calorific value Q of the mixed gas to be measured, calculated by the calorific value calculating portion 305.

Figure 13:
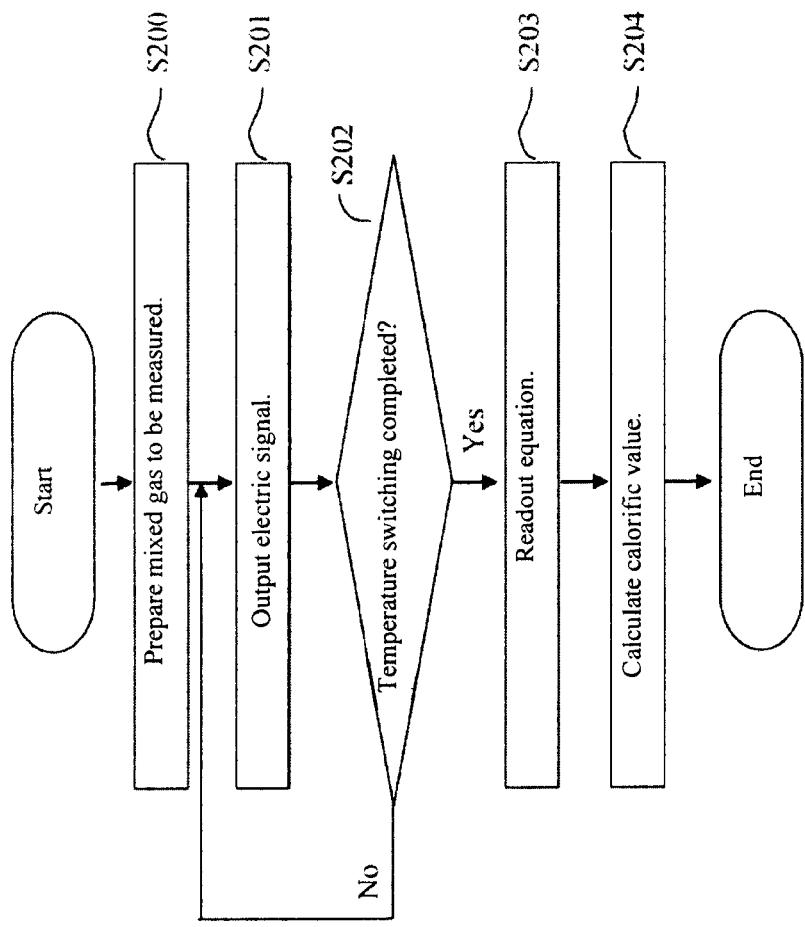
FIG. 13 is a flowchart illustrating a calorific value measuring method as set forth in an example.

The flowchart in FIG. 13 is used next to explain a method for measuring a calorific value as set forth in another example.

(a) In Step S200, the mixed gas to be measured is introduced into the pipe 101 illustrated in FIG. 8. In Step S201, the measuring portion 301 measures the value of the electric signal $S_I$ from the first temperature measuring element 62 that is in contact with the mixed gas to be measured, which is flowing without stopping within the pipe 101, and stores it in the electric signal storage device 401. Following this, the driving circuit 203 applies a driving power $P_{H1}$ to the heater element 61 illustrated in FIG. 1 and FIG. 2, to cause the heater element 61 produce heat at 100° C. The measuring portion 301, illustrated in FIG. 8, stores, into the electric signal storage device 401, the value of the electric signal $S_{H1}(T_{H1})$ from the heater element 61 that is in contact with the mixed gas to be measured, which is flowing without stopping within the pipe 101, and that produces heat at 100° C.

(b) In Step S202, the driving circuit 303, illustrated in FIG. 8, evaluates whether or not the switching of the temperatures of the heater element 61, illustrated in FIG. 1 and FIG. 2, has been completed. If the switching to the temperature of 150° C. and to the temperature of 200° C. has not been completed, then processing returns to Step S201, and the driving circuit 303 applies a driving power $P_{H2}$ to the heater element 61, illustrated in FIG. 1 and FIG. 2, to cause the heater element 61 to produce heat at 150° C. The measuring portion 301, illustrated in FIG. 8, stores, into the electric signal storage device 401, the value of the electric signal $S_{H2}(T_{H2})$ from the heater element 61 that is in contact with the mixed gas to be measured, which is flowing without stopping within the pipe 101, and that produces heat at 150° C.

(c) In Step S202, whether or not the switching of the temperatures of the heater element 61, illustrated in FIG. 1 and FIG. 2, has been completed is evaluated again. If the switching to the temperature of 200° C. has not been completed, then processing returns to Step S201, and the driving circuit 303 applies a driving power $P_{H3}$ to the heater element 61, illustrated in FIG. 1 and FIG. 2, to cause the heater element 61 to produce heat at 200° C. The measuring portion 301, illustrated in FIG. 8, stores, into the electric signal storage device 401, the value of the electric signal $S_{H3}(T_{H3})$ from the heater element 61 that is in contact with the mixed gas to be measured, which is flowing without stopping within the pipe 101, and that produces heat at 200° C.

(d) if the switching of the temperature of the heater element 61 has been completed, then processing advances from Step S202 to Step S203. In Step S203, the calorific value calculating portion 305, illustrated in FIG. 8, reads out, from the equation storage device 402, a calorific value calculating equation having the electric signal $S_I$ from the first temperature measuring element 62 and the electric signals $S_{H1}(T_{H1})$, $S_{H2}(T_{H2})$, and $S_{H3}(T_{H3})$ from the heater element 61 as the independent variables and the calorific value Q of the gas as the dependent variable. Moreover, the calorific value calculating portion 305 reads out, from the electric signal storage device 401, a measured value for the electric signal $S_I$ from the first temperature measuring element 62 that is in contact with the mixed gas to be measured, and measured values for the electric signals $S_{H1}(T_{H1})$, $S_{H2}(T_{H2})$, and $S_{H3}(T_{H3})$ from the heater element 61 that is in contact with the mixed gas to be measured.

(e) In Step S204, the calorific value calculating portion 305 substitutes the respective measured values into the independent variables for the electric signal $S_I$ and the electric signals $S_{H1}(T_{H2})$, $S_{H2}(T_{H2})$, and $S_{H3}(T_{H3})$ of the calorific value calculating equation, to calculate the value of the calorific value Q of the mixed gas to be measured. Thereafter, the calorific value calculating portion 305 stores, into the calorific value storage device 403, the value calculated for the calorific value Q, to complete the method for measuring the calorific value as set forth in this example.

The calorific value calculating method according to the example explained above makes it possible to measure the value of the calorific value Q of a mixed gas to be measured, from the value of the electric signal $S_I$ from the first temperature measuring element 62 that is in contact with the mixed gas to be measured, which is flowing without stopping within the pipe 101, and the values of the electric signals $S_{H1}(T_{H1})$, $S_{H2}(T_{H2})$, $S_{H3}(T_{H3})$ from the heater element 61 that is in contact with the mixed gas to be measured, which is flowing without stopping within the pipe 101, without using expensive gas chromatography equipment or acoustic velocity sensors.

The hydrocarbon compositional ratios of natural gas vary depending on the gas fields from which it is produced. Moreover, natural gas also includes nitrogen ($N_2$) and carbon dioxide gas ($CO_2$), and the like, in addition to the hydrocarbons. Because of this, the volume fractions of the gas components that are included in the natural gas vary depending on the gas field of production, and even if the types of the gas components are known in advance, often the calorific value Q of the natural gas are unknown. Moreover, even with natural gas that derives from the same gas field, the calorific values Q are not always identical, and may Wily depending on the timing of extraction.

Conventionally, when collecting natural gas usage fees, a method was used wherein the charges would be calculated based on the volume used, rather than on the calorific value Q of the natural gas used. However, because the calorific value varies depending on the gas field of production, from which the natural gas is derived, it is not fair to charge based on the volume used. In contrast, the use of the calorific value calculating method according to the present examples makes it possible to calculate easily the calorific value Q of a mixed gas, such as a natural gas, wherein the types of the gas components are known in advance but the calorific value Q are not known because the volume fractions of the gas components are not known. This makes it possible to charge fair usage fees.

Moreover, when driving a gas turbine, there is the need to be able to monitor, without a time lag, the calorific value Q of the natural gas that is the fuel that is supplied to the gas turbine. This is because variations, or the like, in combustion may damage the gas turbine if the calorific value Q of the natural gas is not constant. However, the conventional calorimeter cannot be applied to controlling the calorific value Q of natural gas supplied to a gas turbine because the response time is long, in units of minutes. In this regard, the calorific value measuring system according to the present form of embodiment makes it possible to measure the calorific value in units of seconds, enabling application to controlling the calorific value Q of natural gas that is supplied to a gas turbine.

Furthermore, the calorific value calculating method according to the above makes it easy to know the precise calorific value Q of a mixed gas such as natural gas, thus making it possible to set as appropriate the air flow rate required when burning the mixed gas. This makes it possible to reduce the amount of extraneous carbon dioxide ($CO_2$) emission.

EXAMPLES

First, 23 different sample mixed gases with known values for the calorific value Q were prepared. The 23 different sample mixed gases each included methane ($CH_4$), propane ($C_3H_8$), nitrogen ($N_2$), and/or carbon dioxide gas ($CO_2$) as gas components. For example, a particular sample mixed gas included 90 vol. % methane, 3 vol. % ethane, 1 vol. % propane, 1 vol. % butane, 4 vol % nitrogen, and 1 vol % carbon dioxide. Moreover, a particular sample mixed gas included 85 vol. % methane, 10 vol % ethane, 3 vol % propane, and 2 vol. % butane, and did not include nitrogen or carbon dioxide. Moreover, a particular sample mixed gas included 85 vol % methane, 8 vol % ethane, 2 vol. % propane, 1 vol. % butane, 2 vol. % nitrogen, and 2 vol. % carbon dioxide.

Following this, each of the 23 different sample mixed gases were used to obtain a plurality of measured values for the electric signal $S_I$ from the first temperature measuring element 62, illustrated in FIG. 8, and a plurality of measured values for the electric signals $S_{H1}(T_{H1})$, $S_{H2}(T_{H2})$, $S_{H3}(T_{H3})$, and $S_{H4}(T_{H4})$ from the heater element 61. Thereafter, a linear equation, a quadratic equation, and a cubic equation for calculating the calorific value Q were produced, based on the known values for the calorific values Q of the 23 different sample mixed gases, the plurality of measured values for the electric signals $S_I$ from the first temperature measuring element 62, and the plurality of measured values for the electric signals $S_{H1}(T_{H1})$, $S_{H2}(T_{H2})$, $S_{H3}(T_{H3})$, and $S_{H4}(T_{H4})$ from the heater element 61, with the electric signal $S_I$ from the first temperature measuring element 62 and the values for the electric signals $S_{H1}(T_{H1})$, $S_{H2}(T_{H2})$, $S_{H3}(T_{H3})$, and $S_{H4}(T_{H4})$ from the heater element 61 as the independent variables and the calorific value Q as the dependent variable.

When generating the linear equation for calculating the calorific value Q, it is possible to determine the equation appropriately using between 3 and 5 calibration points. The linear equations generated are given in Equations (33) through (35), below. The respective calorific values Q of the 23 different sample mixed gases were calculated using Equations (33) through (35), and when compared to the true calorific values Q, the maximum error was 2.1%.

$$Q = 40.1 + 17.4 \times V_{H1}(100° C.) + 17.9 \times V_{H2}(150° C.) - 28.9 \times V_{H3}(200° C.) - 10.4 \times V_I \quad (33)$$

$$Q = 40.1 + 23.8 \times R_{H1}(100° C.) + 6.07 \times R_{H2}(150° C.) - 22.8 \times R_{H3}(200° C.) - 11.4 \times R_I \quad (34)$$

$$Q = 40.1 + 17.4 \times AD_{H1}(100° C.) + 17.9 \times AD_{H2}(150° C.) - 28.9 \times AD_{H3}(200° C.) - 10.4 \times AD_I \quad (35)$$

When generating the quadratic equation for calculating the calorific value Q, it is possible to determine the equation appropriately using 8 or 9 calibration points. The respective calorific values Q of the 23 different sample mixed gases were calculated using the quadratic equations that were generated, and when compared to the true calorific values Q, the maximum errors were between 1.2% and 1.4%.

When generating the cubic equation for calculating the calorific value Q, it is possible to determine the equation appropriately using between 10 and 14 calibration points. The respective calorific values Q of the 23 different sample mixed gases were calculated using the cubic equations that were generated, and when compared to the true calorific values Q, the maximum error was less than 1.2%.

Another Example

Figure 14:
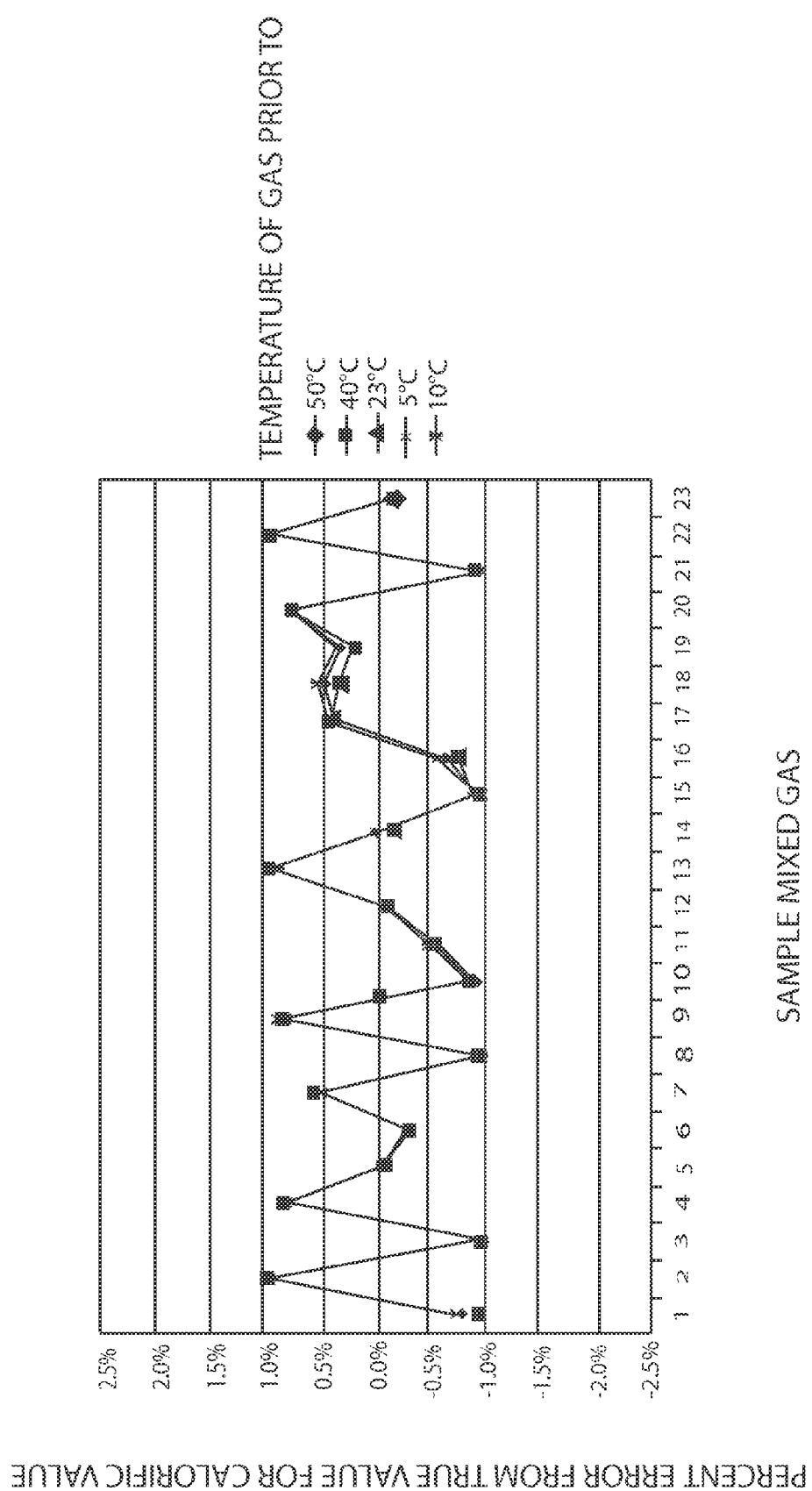
FIG. 14 is a first graph showing the errors from the true values of calorific values calculated for a sample mixed gas relating to an example.
Figure 15:
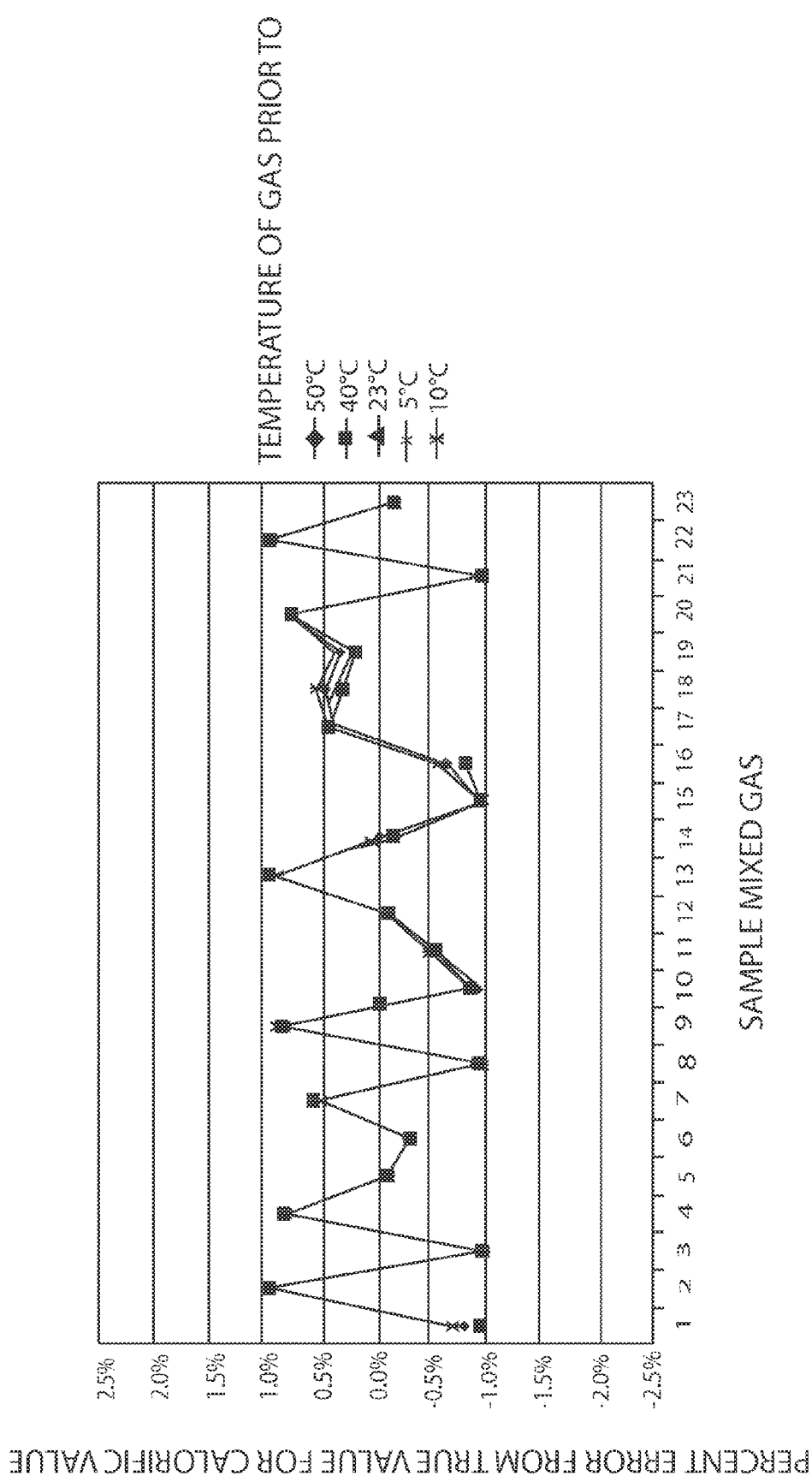
FIG. 15 is a second graph showing the errors from the true values of calorific values calculated for a sample mixed gas relating to another example.
Figure 16:
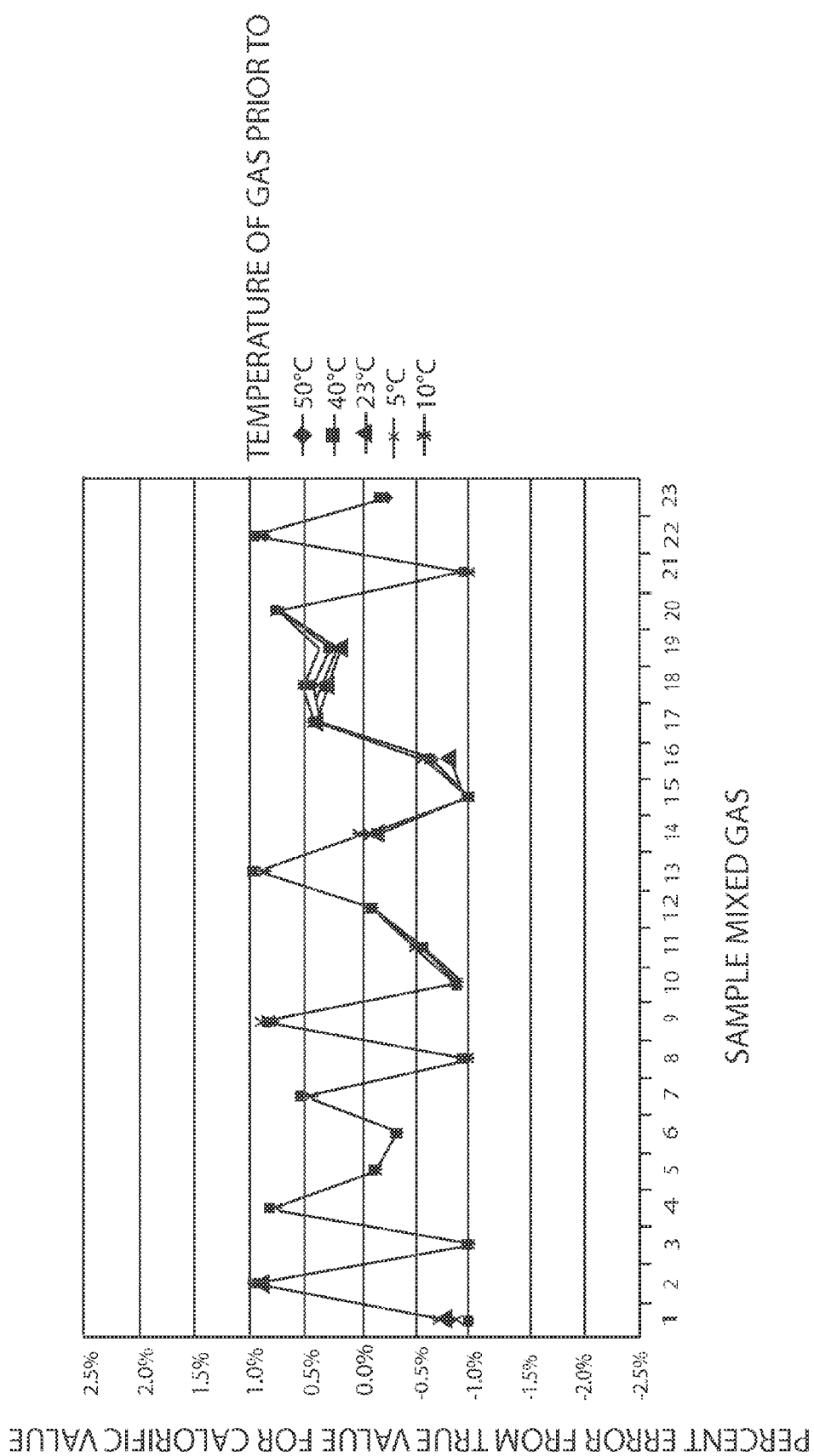
FIG. 16 is a third graph showing the errors from the true values of calorific values calculated for a sample mixed gas relating to a further example.

First, 23 different sample mixed gases with known values for the calorific value Q were prepared in the same manner as with the sample mixed gases used in the above example. Here the temperatures of the sample mixed gases, prior to heating by the heater element 61, were set to −10° C., 5° C., 23° C., 40° C., and 50° C. Following this, a cubic equation for calculating the calorific value was generated having the electric signal $S_I$ from the first temperature measuring element 62 and the electric signals $S_{H1}(T_{H1})$, $S_{H2}(T_{H2})$, and $S_{H3}(T_{H3})$ from the heater element 61 as the independent variables, and the calorific value Q of the gas as the dependent variable. Given this, as illustrated in FIG. 14 to FIG. 16, there was no variability in the error in the calculated calorific value of Q, notwithstanding the temperatures of the sample mixed gases prior to heating by the heater element 61. Note that the result in FIG. 14 was obtained using a resistance R as the electric signal S. The result in FIG. 15 was obtained using a voltage V as the electric signal S. The result in FIG. 16 was obtained using an output signal AD from an A/D converting circuit 304 as the electric signal S.

A Further Example

Figure 17:
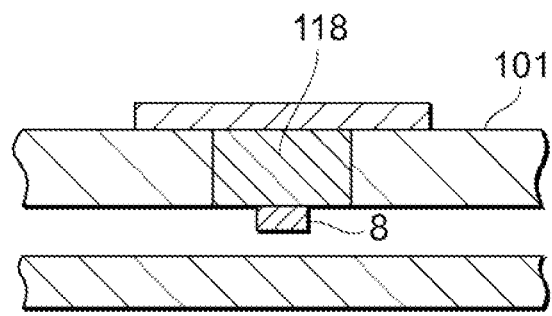
FIG. 17 is a schematic diagram illustrating the arrangement of a microchip as set forth in a yet other example.
Figure 18:
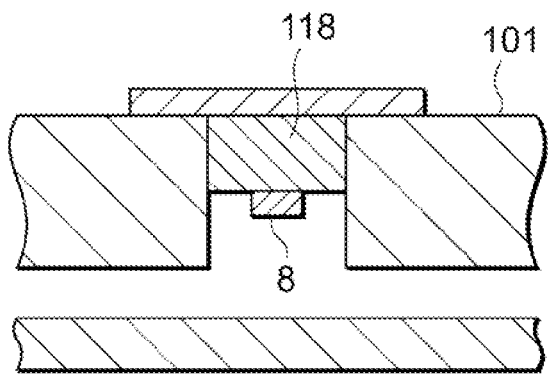
FIG. 18 is a schematic diagram illustrating the arrangement of a microchip as set forth in a comparative example.
Figure 19:
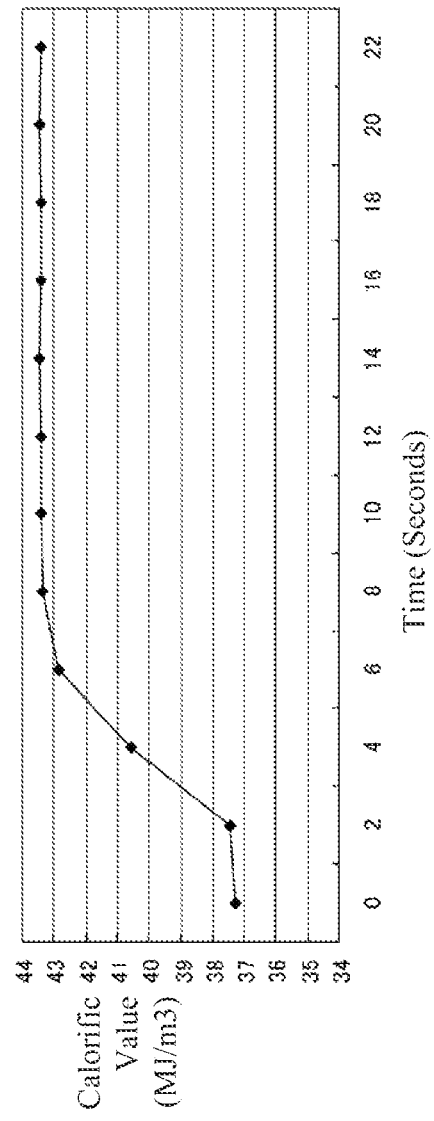
FIG. 19 is a graph illustrating the response speed of a calorific value measuring system as set forth in another example.
Figure 20:
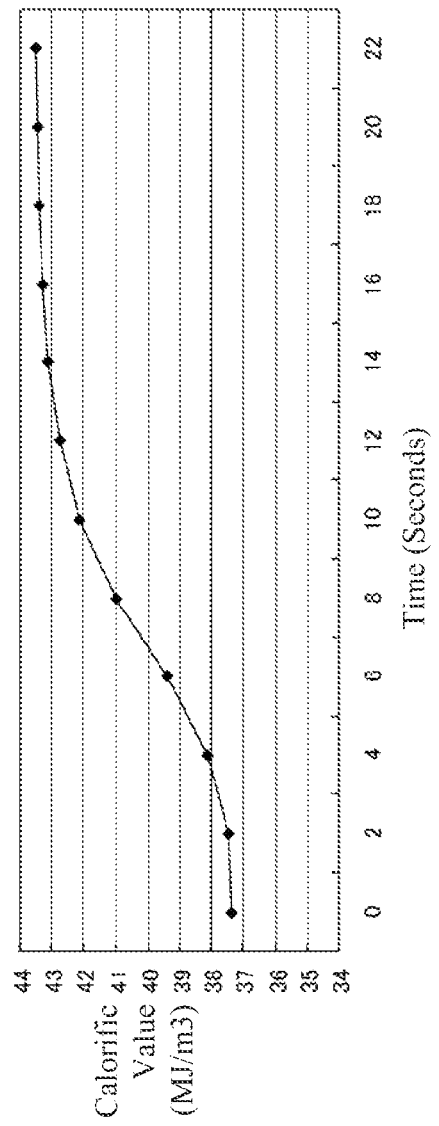
FIG. 20 is a graph illustrating the response speed of a calorific value measuring system as set forth in the comparative example.

As illustrated in FIG. 17, a calorific value measuring system according to an example was prepared wherein the microchip 8 was disposed so as to protrude into the pipe 101. Moreover, as illustrated in FIG. 18, a calorific value measuring system according to a comparative example was prepared wherein a recessed portion was provided in the side wall of the pipe 101 and the microchip 8 was disposed in the recessed portion in the side wall of the pipe 101. Following this, the calorific value calculating system as set forth in the example and the calorific value calculated system as set forth in the comparative example were used to calculate, under identical conditions, the calorific values of the mixed gas to be measured. Given this, as illustrated in FIG. 19, the calorific value measuring system as set forth in this example was able to calculate the calorific value in about 8 seconds. However, as illustrated in FIG. 20, it took about 16 seconds for the calorific value measuring system as set forth in the comparative example was able to calculate the calorific value. Given this, it was demonstrated that disposing the microchip 8 so as to protrude into the pipe 101 improves the response speed of the microchip 8.

Figure 21:
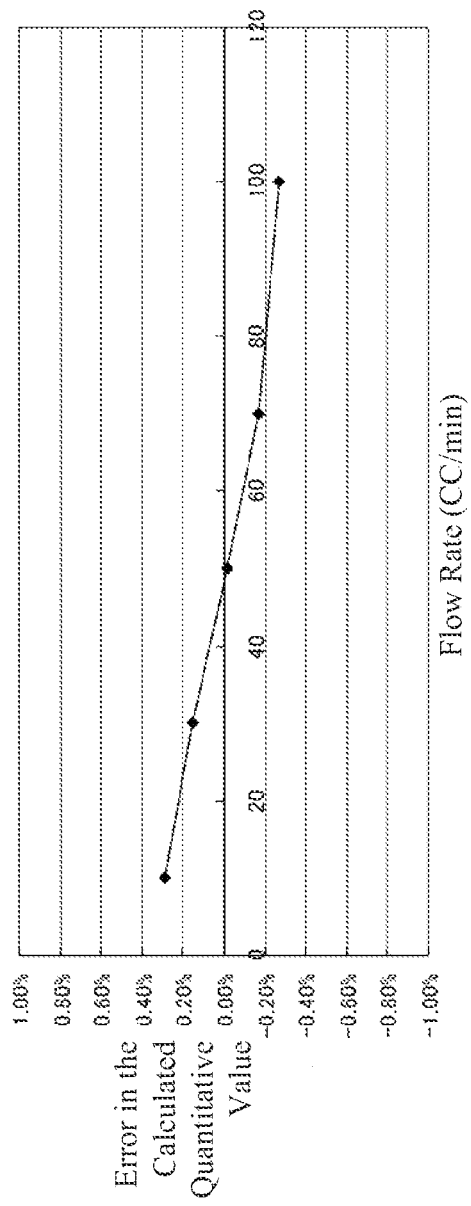
FIG. 21 is a graph showing the relationship between the flow rate of a mixed gas to be measured and the error in the calculated calorific value, in relation to the example of embodiment according to the present invention.

Moreover, the calorific value calculating system as set forth above was used to calculate, under a variety of gas flow rates, the calorific values of the mixed gas to be measured. As a result, as illustrated in FIG. 21, this demonstrated that the calculation error for the calorific value was kept to within 0.3%, even when the flow rate was varied. Consequently, it was demonstrated that the calorific value calculating system as set forth above is able to calculate calorific values precisely, even when in an unfavorable environment wherein the gas flow rates vary, such as in a path for provision to a gas turbine.

While there are descriptions of other examples as set forth above, the descriptions and drawings that form a portion of the disclosure are not to be understood to limit the present invention. A variety of alternate forms of embodiment and operating technologies should be obvious to those skilled in the art. For example, in the present form of embodiment the explanation was for a case wherein the equation storage device 402, illustrated in FIG. 8, stored a calorific value calculating equation wherein an electric signal from a first temperature measuring element 62, illustrated in FIG. 1, and electric signals from a heater element 61 at a plurality of different heat producing temperatures are the independent variables and the calorific value Q is the dependent variable.

In contrast, as explained in Equation (22), above, the calorific value Q, can be obtained from an equation wherein the radiation coefficients $M_{I1}(T_{H1})$, $M_{I2}(T_{H2})$, and $M_{I3}(T_{H3})$ of the gas at the respective temperatures $T_{H1}$, $T_{H2}$, and $T_{H3}$ for the heater element 61 are the variables. As a result, the equation storage device 402, illustrated in FIG. 8, may store a correlation between the radiation coefficients and the calorific value Q of a calorific value calculating equation wherein the radiation coefficients of the gas at a plurality of heat producing temperatures of the heater element 61 are the independent variables and the calorific value Q is the dependent variable. In this case, the measuring portion 301 measures the measured values for the radiation coefficients of the gas that is injected into the pipe 101, doing so with the heater element 61 producing heat at a plurality of heat producing temperatures. Note that as was explained for Equation (9), above, it is possible to measure the radiation coefficients of the gas using a microchip 8. The calorific value calculating portion 305 substitutes the measured value for the pressure of the gas and the measured values for the radiation coefficients of the gas into the independent variables in the calorific value calculating equation stored in the equation storage device 402, to calculate the measured value for the calorific value Q of the gas.

Figure 22:
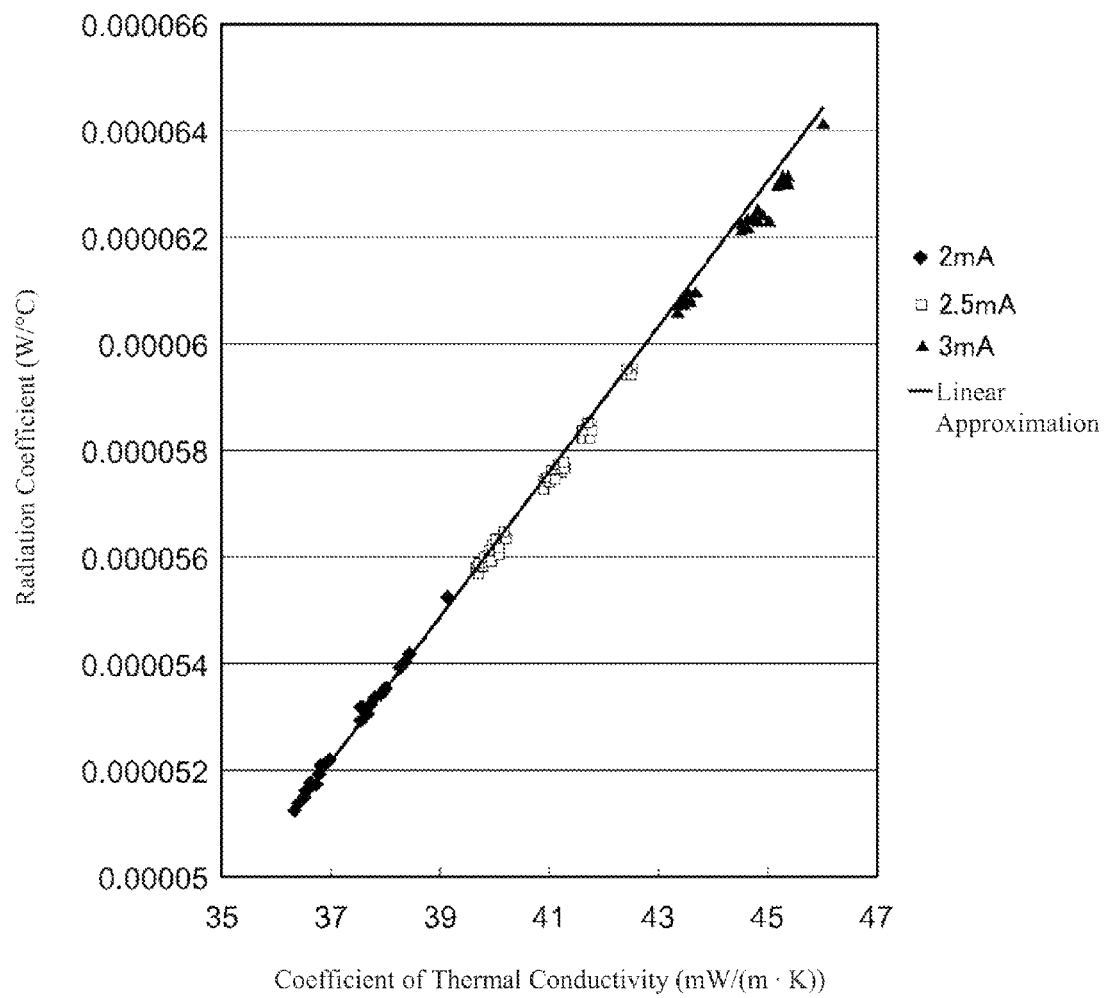
FIG. 22 is a graph illustrating the relationship between the gas thermal conductivity and heat loss coefficient in another form of example.

FIG. 22 illustrates the relationship between the radiation coefficient and the thermal conductivity in a mixed gas when electric currents of 2 mA, 2.5 mA, and 3 mA are produced in a heat producing resistance. As illustrated in FIG. 22, typically there is a proportional relationship between the radiation coefficient and the thermal conductivity of the mixed gas. As a result, the equation storage device 402, illustrated in FIG. 8, may store a calorific value calculating equation wherein the thermal conductivities of the gas at a plurality of heat producing temperatures of the heater element 61 are the independent variables and the calorific value Q is the dependent variable. In this case, the measuring portion 301 measures the measured values for the thermal conductivities of the gas that is injected into the pipe 101, doing so with the heater element 61 producing heat at a plurality of heat producing temperatures. The calorific value calculating portion 305 substitutes the measured value for the pressure of the gas and the measured values for the thermal conductivities of the gas into the independent variables in the calorific value calculating equation stored in the equation storage device 402, to calculate the measured value for the calorific value Q of the gas.

In this way, the present invention should be understood to include a variety of forms of embodiment, and the like, not set forth herein.

The invention claimed is:
1. A calorific value measuring system, comprising:
    a pipe wherein a fluid flows;
    a flow rate controlling device controlling a flow rate of the fluid that flows with in the pipe;
    a temperature measuring element disposed within the pipe;
    a heater element, disposed within the pipe, producing heat at a plurality of heat producing temperatures;
    a measuring portion measuring a value for an electric signal from the temperature measuring element that is dependent on a temperature of the fluid that is flowing within the pipe, and a value for an electric signal from the heater element at each of the plurality of the heat producing temperatures;
    an equation storage device storing a calorific value calculating equation that uses an electric signal from the temperature measuring element and electric signals from the heater element at the plurality of the heat producing temperatures as independent variables and uses a calorific value as the dependent variable; and
    a calorific value calculating portion reading out the calorific value calculating equation from the equation storage device and calculating a value for the calorific value of the fluid through substituting the value of the electric signal from the temperature measuring element and the value of the electric signal from the heater element into the independent variables of the calorific value calculating equation.

2. The calorific value measuring system as set forth in claim 1, wherein:
    the temperature measuring element and the heater element are disposed so as to protrude into the pipe.

3. The calorific value measuring system as set forth in claim 1, wherein:
    the temperature measuring element and the heater element are disposed so as to protrude into the pipe at an angle so as to face the fluid that is flowing within the pipe.

4. The calorific value measuring system as set forth in claim 1, wherein:
    the fluid is a natural gas.

5. The calorific value measuring system as set forth in claim 1, wherein:
    the fluid is a gas.

6. The calorific value measuring system as set forth in claim 1, further comprising:
    an electric signal storage device storing the value of the electric signal from the temperature measuring element and the value of the electric signal from the heater element, measured by the measuring portion, wherein
    the calorific value calculating portion calculates the value for the calorific value of fluid using the value of the electric signal from the temperature measuring element and the value of the electric signal from the heater element, stored in the electric signal storage device.

7. The calorific value measuring system as set forth in claim 1, wherein:
   the calorific value calculating equation is generated based on calorific values for a plurality of sample mixed fluids that include a plurality of types of fluid components, and respective values for electric signals from the heater element that contacts the plurality of the sample mixed fluids.

8. The calorific value measuring system as set forth in claim 7, wherein:
   support vector regression is used in order to generate the calorific value calculating equation.

\* \* \* \* \*